United States Patent [19]
Osinga et al.

[11] Patent Number: 5,858,764
[45] Date of Patent: *Jan. 12, 1999

[54] YEAST STRAINS FOR SACCHARIDE FERMENTATION

[75] Inventors: Klaas Anne Osinga, Voorschoten; Robert Franciscus Beudeker, Delft; Johannes Sertus Van der Plaat, Leiderdorp; Johannes Abraham de Hollander, Oegstgeest, all of Netherlands

[73] Assignee: Gist-Brocades, Delft, Netherlands

[*] Notice: The term of this patent shall not extend beyond the expiration date of Pat. No. 5,190,877.

[21] Appl. No.: 641,181

[22] Filed: Oct. 4, 1995

Related U.S. Application Data

[63] Continuation of Ser. No. 974,871, Nov. 12, 1992, abandoned, which is a continuation of Ser. No. 615,328, Nov. 19, 1990, abandoned, which is a continuation of Ser. No. 241,022, Sep. 1, 1988, abandoned, which is a continuation-in-part of Ser. No. 140,031, Dec. 31, 1987, abandoned, said Ser. No. 974,871, is a continuation of Ser. No. 611,319, Nov. 13, 1990, Pat. No. 5,190,877, which is a continuation of Ser. No. 140,031, Dec. 31, 1987, abandoned.

[30] Foreign Application Priority Data

Sep. 3, 1987 [EP] European Pat. Off. .............. 87201670
Mar. 9, 1988 [EP] European Pat. Off. .............. 88200453

[51] Int. Cl.$^6$ .............................. C12N 1/19; C12N 1/18; C12N 15/56; C12N 15/81
[52] U.S. Cl. .................................. 438/854.2; 435/172.3; 435/254.21; 435/254.3; 435/320.1
[58] Field of Search .............................. 435/172.3, 254.3, 435/254.2, 254.21, 320.1

[56] References Cited

U.S. PATENT DOCUMENTS

| | | | |
|---|---|---|---|
| 4,370,420 | 1/1983 | Clement et al. | 435/254.21 |
| 4,396,632 | 8/1983 | Clement et al. | 426/62 |
| 4,778,761 | 10/1988 | Miyanohara et al. | 435/320.1 |
| 5,190,877 | 3/1993 | Osinga et al. | 435/256 |

FOREIGN PATENT DOCUMENTS

| | | |
|---|---|---|
| A-0128524 | 6/1984 | European Pat. Off. . |
| 0163491 | 12/1985 | European Pat. Off. . |
| A-0206571 | 6/1986 | European Pat. Off. . |
| 989247 | 4/1965 | United Kingdom . |
| 1539211 | 1/1979 | United Kingdom . |
| A-2155935 | 2/1984 | United Kingdom . |
| A-2178431 | 7/1986 | United Kingdom . |
| WO 86/07091 | 4/1986 | WIPO . |

OTHER PUBLICATIONS

Ammerer, G., *Methods Enzymol.*, (1983) 101: 192–210.
Burrows, S., In: *The Yeasts*, vol. 3– Yeast Technology., (1971) 3: 349–420.
Federoff et al., *J. Bacteriol.*, (1982) 149: 1064–1070.
Hadfield et al., *Gene.*, (1986) 45: 149–158.
Rodicio & Zimmerman, *Curr. Genet.*, (1985) 9: 547–551.
Innis et al., *Science.*, (1985) 228: 21–26.
Orr–Weaver et al., *PNAS USA.*, (1981) 78:6354–6358.
Panchal et al., *Curr. Genet.*, (1987) 12: 15–20.
Parent et al., *Yeast.*, (1985) 1: 83–138.
Reipen et al., *Curr. Genet.*, (1982) 6:189–193.
Rodicio, R., *Mol. Gen. Genet.*, (1984) 197: 491–496.
Rodicio & Zimmerman, *Curr. Genet.*, (1985) 9: 539–545.
Rodicio & Gascon, *XI international Specialized Symposium on Yeasts– Regulation of Transport and Metabolism in Yeasts–Basic Biotachnological Aspects.*, (1986) p. 51.
Rodicio, R., *Curr. Genet.*, (1986) 11: 235–241.
Rudolph et al., *Gene.*, (1985) 36: 87–95.
Seiler, D., *Yeast Spoilage of Bakery Products.*, (1980) 9: 135–152.
Thomsen, K., *Carlsberg Res. Commun.*, (1983) 48: 545–555.
Cohen et al., *Mol. Gen. Genet.*, (1985) 200: 1–8.
Hong et al., *Mol. Cell Biol.*, (1985) 7: 2477–2483.
Charron et al., *Genetics.*, (1987) 166: 23–31.
Nagata et al., *EMBO J.* (1984) 3: 1825–1830.
Hitzeman et al., *Nature.*, (1981) 293: 717–722.
Tubb, R., *Brewers' Guardian.*, (1984) 113: 34–37.
Scherer et al., *PNAS USA.*, (1979) 76: 4951–4955.
Gottlin–Ninfa et al., *Mol. Cell. Biol.*, (1986) 6: 2185–2197.
Sreekrishna et al., *PNAS USA.*, (1985) 82: 7910–7913.
Needleman et al., *PNAS USA.*, (1984) 81: 2811–2815.
Hong et al., *Gene.*, (1986) 41: 75–84.
Stewart, *Canadian Journal of Microbiology.*, (1981) 27: 973–990.
Panchal et al., *food Technology.*, (1984) Feb. 1984: 99–106, 111.
Rothstein, *Methods in Enzymology.*, (1983) 101: 202–211.
Mowshowitz, J., *J. Bact.*, (1979) 137: 1200–1207.
Needleman et al., Proc. Natl. Acad. Sci. 81, 2811–2815, May 1984.
Stewart, Can. J. Microbiol., 27, 973–9990, 1981.
Hong et al., Mol. Cell. Biol., 7 (7), 2477–2483, Jul. 1987.
Nagata et al., EMBO Journal, 3, (8), 1825–1985, 1984.
Rothstein, Meth. Enzym., 101, 202–211, 1983.

(List continued on next page.)

Primary Examiner—Nancy Degen
Attorney, Agent, or Firm—McDonnell Boehnen Hulbert & Berghoff

[57] ABSTRACT

New yeast strains providing for an enhanced rate of the fermentation of sugars, and a process to obtain such yeasts and the use of these yeasts. Yeasts capable of improved fermentation of sugars, a process to obtain these yeasts and the use of these yeasts are provided. The yeasts show higher rates of metabolism resulting in for example higher carbon dioxide and ethanol production in media containing sugars, such as maltose, as main carbon and energy source. The fermentation rate of sugars is improved by the introduction into a yeast of one or more DNA constructs comprising at least one gene encoding a protein promoting the uptake and/or initial metabolic conversion of a transported sugar substrate.

45 Claims, 23 Drawing Sheets

OTHER PUBLICATIONS

Panchal et al., Curr. Genet., 12, 15–20, 1987.
Weaver et al., Proc. Natl. Acad. Sci., 78 (10), 6354–6358, Oct. 1981.
Cottrelle et al., J. of Biol. Chem, 1985, 260:3090–3096.
Goldenthal et al., Mol. Gen. Genet. 209:508–517, 1987.
Hautera and Lovgren, J. Inst. Brew., 81:309–313, 1975.
Johnston et al., Proc. Natl. Acad. Sci. USA, 1982, 79:6971–6975.
Lovgren and Hautera, European J. Appl. Microbiol. 4:37–43, 1977.
Nagata et al., EMBO J. 3:1825–1830, 1984.
Suomalainen et al., Process Biochemistry 7:16–22, 1972.
Trivedi et al., CRC Critical Reviews in Biotechnology, 1986, 4(1):75–109.

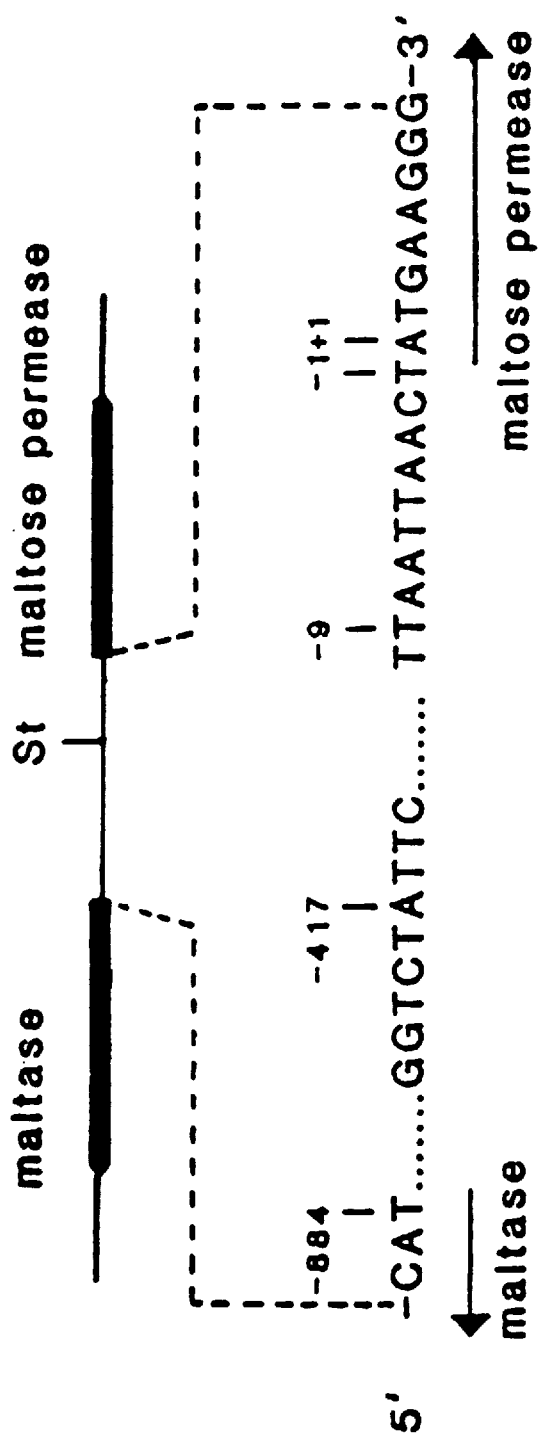
Figure 5a
Figure 5b

YEAST STRAINS FOR SACCHARIDE FERMENTATION

CROSS-REFERENCE TO RELATED APPLICATIONS

This application is a continuation of U.S. application Ser. No. 07/974,871 filed Nov. 12, 1992 now abandoned, which is a continuation of U.S. application Ser. No. 07/615,328 filed Nov. 19, 1990 (now abandoned) which is a continuation of U.S. application Ser. No. 07/241,022 filed Sep. 1, 1988 (now abandoned) which is a continuation-in-part of U.S. application Ser. No. 07/140,031 filed on Dec. 31, 1987 (now abandoned). U.S. application Ser. No. 07/974,871, filed Nov. 12, 1992, is a continuation of U.S. application Ser. No. 07/611,319 (now issued as U.S. Pat. No 5,190,877) filed on Nov. 13, 1990 which is a continuation of U.S. application Ser. No. 07/140,031 filed Dec. 31, 1987, now abandoned.

New yeast strains providing for an enhanced rate of the fermentation of sugars, a process to obtain such yeasts and the use of these yeasts.

The invention relates to new yeasts capable of improving the fermentation of sugars, to a process to construct such yeasts and to the use of these improved yeasts.

It is well known that yeast strains belonging for example to the genus Saccharomyces are capable of fermenting sugars to approximately equimolar amounts of $CO_2$ and ethanol under anaerobic conditions. The leavening activity of yeast in dough is a result of this fermentation. The commercial product baker's yeast exists in several formulations comprising compressed yeast or fresh yeast and dried yeast. Dried yeast is available as active dry yeast and as instant dry yeast with moisture contents of about 6–8% and 3–6%, respectively.

One of the early steps in the metabolism of sugars by the action of yeast is the transport of the sugar molecules across the plasma membrane. Specific carriers for different sugars are espressed in yeast. The uptake of maltose, for example, is dependent on the presence of a specific maltose permease. This carrier may exist in two forms distinguished by differences in maximal velocity (Vmax) and affinity constant (Km) (A. Busturia and R. Lagunas, Biochim. Biophys. Acta 820, 324 (1985)). The translocation of maltose across the yeast plasma membrane is coupled to the electrochemical proton gradient in this membrane. For every maltose molecule taken up one proton is symported (R. Serrano, Eur. J. Biochem, 80, 97 (1977)).

Intracellularly, maltose is hydrolyzed to two molecules of glucose in a reaction catalyzed by maltase (alpha-glucosidase). Glucose is subsequently converted to carbon dioxide and ethanol via the Embden-Meyerhof pathway. In comparison with the fermentation of glucose two additional enzymes are required for the fermentation of maltose viz. maltose permease and maltase. The synthesis of these enzymes is induced by maltose and repressed by glucose, fructose or mannose. In non-sugared ("lean") doughs maltose is the most abundant sugar available to yeast. In case sucrose is added to the dough this disaccharide is hydrolyzed extracellularly by yeast to glucose and fructose. Subsequently these hexoses are taken up by yeast by action of distinct permeases.

It is generally found that addition of sucrose to media containing maltose, as for example dough, inhibits the metabolism of maltose by yeast cells. This is due to the fact that transcription of genes encoding maltose permease and maltase is represented by glucose (R. B. Needleman, D. B. Kaback, R. A. Dubin, E. L. Perkins, N. G. Rosenberg, K. A. Sutherland, D. B. Forrest and C. A. Michels, Proc. Natl. Acad. Sci. USA 81, 2811 (1984)).

Genes required for the uptake and hydrolysis of maltose are clustered in a MAL-locus (R. B. Needleman et al. Supra). Strains of Saccharomyces may contain up to five MAL-loci (MAL 1–4 and MAL 6), which are unlinked and located at the telomers of different chromosomes (J. L. Celenza and M. Carlson Genetics 109, 661–664 (1985)). A MAL-locus comprises genes encoding maltose permease, maltase and one or more regulatory proteins (MAL regulator) required for the induction by maltose (R. B. Needleman et al. Supra; J. D. Cohen, M. J. Goldenthal, T. Chow, B. Buchferer and J. Marmur, Mol. Gen. Genet. 200, 1 (1985); R. A. Dubin, E. L. Perkins, R. B. Needleman and C. A. Michels, Mol. Cell. Biol. 6, 2757 (1986)). Said genes have been isolated and cloned (A. O. J. D. Cohen et al., supra; R. B. Needleman et al., Supra; H. J. Federoff, J. D. Cohen, T. R. Eccleshall, R. B. Needleman, B. A. Buchferer, J. Giacalone and J. Marmur, J. Bacteriol. 149, 1064 (1982)).

As mentioned above yeast fermentation in lean dough depends on maltose as main substrate. Maltose is produced in the dough from starch by action of amylases, which are normally present in the flour. In addition, the flour contains a variable amount (0–0.5) free sugars like glucose, raffinose etc. (H. Suomalafnen, J. Dettwiler and E. Sinda, Process Biochem. 7, 16 (1972)). These sugars are rapidly consumed by the yeast. Several studies have been published investigating the possible correlation between maltose fermentation and leavening activity of baker's yeast. In some cases a positive correlation was found between the rate of maltose fermentation with activities of maltase and maltose permease. However a positive correlation between the activities of maltase and maltose permease with leavening ability in lean dough could not be observed (P. Hautera and T. Lövgren, J. Inst. Brew. 81, 309 (1975); T. Lövgren and P. Hautern, Eur. J. Appl. Microbiol. 4, 37 (1977)).

Transformation of yeast cells with multicopy plasmids containing genes encoding maltase and maltose permease yielded a fourfold increase in specific activity of maltase but maltose permease activity was not enhanced. Introduction of extra genes encoding the regulatory protein did result in a moderate increase in specific activity of maltase but again no effect was observed on maltose permease activity (J. D. Cohen et al., Supra). Obtained transformants were not assayed for carbon dioxide or ethanol production by these investigators. In fact prior art discouraged performing such tests since it had been shown repeatedly that there was no correlation between activities of maltose permease and maltase with carbon dioxide production (leavening activity) in lean dough (H. Suomalainen, J Dettwiler and E. Sinda, Supra; H. Suomalainen, Eur. J. Appl. Microbiol, 1, 1 (1975); P. Hautera and T. Lövgren, supra; T. Lövgren and P. Hautera, Supra).

We have now found that yeasts, transformed by integrative plasmids of which examples will be described hereinafter, shown an enhanced level of maltose permease and maltase activity, compared to the untransformed strain. These enhanced maltase and maltose permease activities surprisingly coincide with an increase of $CO_2$ production of leavening activity, as was also observed in case of yeast transformed with episomal vectors.

These improved yeasts show higher rates of metabolism resulting in for example higher carbon dioxide and ethanol production in media containing sugars, such as maltose, as main carbon and energy source. The methods provided involve application of recombinant DNA techniques in such a way that the rate of maltose fermentation by said yeasts is increased drastically irrespective of the presence of other sugars as for example glucose.

Furthermore these improved yeast strains show a excellent leavening activity (gas production) in dough. Analogously, the higher rate of ethanol production of these yeasts will result in a reduced fermentation time for yeast employed in the production of potable and industrial alcohol or a larger amount of alcohol produced in a certain time. Furthermore in case (accumulation of) maltose is inhibiting enzymes, which convert sugar or starch, rapid removal of maltose is advantageous for said fermentation process. By applying the process of the present invention a yeast can be obtained in which (an) extra gene(s) is (are) introduced encoding maltase and/or maltose permease.

The present invention provides a transformed yeast and a process to produce said yeast improved in the fermentation rate of sugars which comprises the introduction into yeast of at least one, preferably homologous, DNA construct which comprises at least one gene in said yeast encoding a protein promoting the uptake and/or initial metabolic conversion of a transported substrate, the gene being capable of expression in said yeast. The rate of fermentation of sugars can be improved during several phases of the leavening, for example an enhanced rate caused by the fermentation of maltose or sucrose.

By homologous DNA is meant DNA originating from the same yeast genus. For example Saccharomyces is transformed with DNA originating from Saccharomyces. In this way it is possible to improve already existing properties of the yeast genus, without introducing new properties, which were not present in the genus before. The improvement of fermentation rate of sugars may be obtained under aerobic and/or anaerobic conditions. The genes of interest include permeases, particularly maltose permease, saccharidases, particularly maltase, kinases, particularly hexokinases and glucokinase, and the like. This invention may be applied, for example, for a carrier protein required for the uptake of glucose or fructose and hexokinases and glucokinase which catalyze the initial intracellular metabolic conversion of these hexoses to hexose phosphates.

The present invention also provides efficient methods for introduction into the yeasts of at least one homologous DNA construct.

Advantageously the invention may be applied to a construct which comprises at least one gene which encodes a protein which promote the uptake of maltose and the initial metabolic conversion of maltose to glucose. In this way yeasts can be obtained which have several advantages in comparison with the original (host) strains. The benefits of such improved yeast may be found particularly in the improved ethanol and $CO_2$ production. For example when the invention is applied to baker's yeast this will be an enormous advantage for a baker because the baker requires less time or less yeast in order to develop lean dough because of the improved leavening activity of the novel strains.

It will be appreciated that the transformed yeast according to the invention can be used as starting strain in strain improvement procedures other than DNA mediated transformation, for instance, protoplast fusion, mass mating and mutation. The resulting strains are considered to form part of the invention.

According to a preferred embodiment of the invention the novel strains will consume substantial amounts of maltose in the presence of glucose. Therefore bakers may save on sugar expenses as well, since less sugar needs to be added to obtain sweet doughs.

It is well-known that osmotolerant yeasts show a poor performance (leavening activity) in lean dough. By osmotolerant yeasts is meant yeast which have a good performance in sweet doughs. Doughs for sweet bakery goods will contain for example 10–30% sugar (based on flour weight). Therefore, when an osmotolerant strain is chosen as a host to be tranformed according to the invention an osmotolerant yeast is obtained which not only is applicable in sweet doughs but may also be used in lean dough since its capacity to ferment maltose is improved according to the invention. As a consequence the baker conveniently requires only one type of yeast both for sweet doughs and for lean doughs.

The need for yeast strains that have a good performance in lean as well as in sweet doughs is for example described in EP-A-128524 and DE-A-2757778. To obtain yeast strains which have a good performance in sugar rich and lean dough, EP-A-I28525 describes a protoplast fusion method: DE-A-2757778 describes in order to obtain such yeast strains a selection method of strains from a population if diploid strains prepared by hybridization or mutation methods. Both procedures need a lot of experimentation and the results are unpredictable and not reproducible. By using the process of the present invention, controlled and reproducible results with the transformed yeast strains can be obtained. The testing of the strains produced according to the invention can be minimal because the properties of the strain itself are substantially not altered except for the improved properties as disclosed.

The present invention provides a compressed yeast which shows a gas production of at least 340 ml/285 mg dry weight of yeast in 165 minutes in Test B and a gas production of at least 170 ml/285 mg dry weight of yeast in Test B'. Tests B and B' are described hereinafter. Preferably the compressed yeast shows a gas production of 380–450 ml/285 mg dry weight of yeast in 165 minutes in Test B and 180–240 ml/285 mg dry weight of yeast in Test B' and more preferably at least 400 ml/285 mg dry weight of yeast in Test B and at least 190 ml/285 mg dry weight of yeast in Test B', respectively. Advantageously instant dry or active dry yeast is prepared from this compressed yeast. During drying of the compressed yeast generally 15–25% of the leavening activity based on dry matter is lost. The present invention also provides a dried yeast (3–8 wt % moisture) which shows a gas production of 310–360 ml/285 mg dry weight of yeast in 165 minutes in Test C and 145–195 ml/285 mg dry weight of yeast in Test C' and preferably at least 330 ml/285 mg dry weight of yeast in Test C and at least 155 ml/285 mg dry weight of yeast in Test C', respectively. The gas values obtained with yeast prepared according to the invention have never been found even when commercially available strains were tested in Tests C and C'. The invention can also be applied for yeasts which show a good performance in leavening activity in the range of 0–6 or 0–10% sugar dough. In this way it is possible to prepare compressed yeasts which show a gas production of 400–500 ml/285 mg dry weight of yeast in 165 minutes in Test B, preferably these compressed yeasts show a gas production of at least 440 ml/285 mg dry weight of yeast. Dried yeasts can then be obtained which show a gas production of 320–400 ml/285 mg dry weight of yeast in 165 minutes in Test C, preferably the dried yeast shows a gas production of at least 350 ml/285 mg dry weight of yeast.

Similar advantages of these novel strains are found in fermentations for the production of potable and industrial alcohol.

Since the overall metabolic rate of these novel strains has been increased when maltose serves as a substrate the overall production rate of metabolites such as glycerol and aroma compounds will be increased as well.

In one aspect of the invention vectors are provided bearing a DNA construct encoding one or more proteins involved in maltose fermentation. The present invention also provides a microbial host, preferably a yeast, which is, for example, a species of Saccharomyces transformed with vectors disclosed by the invention. These vectors may be self-replicating and contain advantageously a gene, or combinations of genes, selected from those encoding maltose permease, maltase and maltose regulatory protein. Surprisingly, it has been found that yeast, transformed with such vectors, shows an enhanced rate of maltose fermentation, which results in an increased rate of $CO_2$ production in dough. These additional genes are located on episomes, however, and it is known from literature that such extrachromosomal molecules are easily lost during non-selective propagation (i.e. growth in the absence of G418 in this particular case) (C. D. Hollenberg (1982) Gene Cloning 12, Organisms other than *E. coli,* Eds. P. H. Hofschneider, W. Goebel, Springer Verlag, 119; S. A. Parent, C. M. Fenimone, and K. A. Bostian (1985), Yeast 1, 83). From a practical point of view it is preferred to cultivate yeast non-selectively and therefore a set of integrating plasmids containing, preferably altered, maltase and/or maltose permease genes are advantageously constructed. By "altered" is meant the exchange of the natural promoter by another promoter, preferably homologous. In case processes are developed which allow stable proliferation of plasmids in the absence of a selective pressure, integration of newly introduced DNA is not a prerequisite anymore in order to obtain stable transformants.

It is known from literature that one cell contains between 20–100 molecules of these extra plasmids (C. D. Hollenberg (1982), Supra; A. Takagi, E. N. Chun, C. Boorchird, S. Harashima and Y. Oshima, Appl. Microbiol. Biotechnol. 23, 123; J. Mellor, M. J. Dobson, N. A. Roberts, N. J. Kingsman and S. M. Kingsman (1985) Gene 33, 215).

The level of expression of episomal genes may be increased even further by exchange of the original promoters by stronger promoters. It seems likely that in the future it will be possible to allow stable replication of plasmids in the absence of a selective pressure.

The maltase and/or maltose permease genes are according to the invention advantageously integrated into the yeast chromosome via transformation with linear plasmids (see T. L. Orr-Weaver, J. W. Szostak, R. Rothstein (1981) Proc. Natl. Acad. Sci. U.S. A. 78, 6354). The obtained yeasts are stable transformants, i.e. altered maltase and/or maltose permease genes can be maintained in the genome even in the absence of selective pressure.

It is known, that during integration only one or a few copies of genes located on a plasmid become integrated into the chromosome. Therefore, in order to obtain similar improvements in $CO_2$ production as obtained when episomal vectors are used, the level of gene expression may be advantageously altered by application of strong constitutive promoters, not sensitive to glucose repression. Such promoters are preferred in order to compensate for the difference in gene copy number between yeast transformed with episomal and with integrative vectors, and in order to prevent the effects of glucose-repression. It is observed, for instance, that during the first 30–40 minutes of fermentation in media containing maltose as main carbon and energy source and relatively low concentrations of glucose, mRNA levels of maltose permease and maltase decline to barely detectable levels. Once the glucose has been consumed, induction of gene expression by maltose results in a rapid increase in both mRNA levels.

As indicated, the genes may be used with their natural or wild-type promoter or the promoter may be substituted with a different promoter, preferably a homologous promoter. Particularly, where the wild-type promoter is regulatable or inducible, it may be desirable to provide for constitutive transcription, or a stronger or weaker promoter. Conversely, where the wild-type promoter is constitutive, it may be of interest to provide for a regulatable or inducible promoter or a stronger or weaker promoter.

Desirably, strong promoters will be employed, particularly where there may be a relatively low copy number of the construct in the host. Strong promoters will normally be those involved with the production of proteins produced at a high level during the life cycle of the yeast or where regulatable, at some period of interest in the life cycle of the yeast, as related to the subject invention.

Promoters associated with the glycolytic cycle of yeast are of particular interest, which include alcohol dehydrogenase I and II, phosphoglucoisomerase, glucose-6-phosphate dehydrogenase, triose phosphate isomerase, glyceraldehydephosphate dehydrogenase, phosphoglycerate kinase, enolase, phosphoglyceromutase, pyruvate kinase, and lactate dehydrogenase. Other promoters involved with proteins produced in high amount, include promoters associated with ribosomal expression, such as promoters for the transcription of initiation factors, elongation factors, and the like. Particular elongation factors include EF-1 and EF-2, etc.

Of particular interest is the use of promoters in combination with structural genes involved with maltose metabolism, particularly maltase, maltose permease and MAL-regulator. These promoters may be constitutive or regulatable, so long as the promoter is induced during the fermentation of the sugar. For example, many of the glycolytic promoters are activated in the presence of a sugar or a sugar metabolite, such as ethanol. Thus, promoters such as alcohol dehydrogenase will be active during the leavening of flour. Similarly, those promoters associated with cell proliferation will also be active during the leavening of dough. Furthermore, by providing for promoters which are not regulated by the MAL regulator, the yeast may be used in the presence of glucose, without repression. In addition, the genes do not require maltose for induction.

Where the wild-type promoters are employed in conjunction with the structural genes of interest, it may be desirable to provide for enhanced production of a regulatory protein. In this way, the regulatory protein may be maintained at a high level, when the inducer is present. For example, in the presence of maltose, the MAL regulatory protein will be expressed at a high level, so as to provide for expression of the other proteins associated with maltose metabolism and regulated by the MAL regulatory protein.

The alterations in gene expression, as described in detail in the experimental procedures, comprise the exchange of the original promoters plus (part of) the untranslated leader sequences for those of alcohol dehydrogenase I (ADHI) and translation elongation factor EF1αA preferably derived from the host yeast, for example Saccharomyces. As a consequence, expression will become insensitive to glucose repression and independent of maltose for induction.

It has been found that yeasts, transformed by these integrative plasmids show an enhanced level of maltose permease and maltase activity compared to the untransformed strain. These enhanced maltase and maltose permease activities surprisingly coincide with an increase of $CO_2$ production or leavening activity, as was also observed in case of yeast transformed with episomal vectors.

The obtained improvement in leavening activity is maintained during storage even at elevated temperatures, for example, at 20°–25° C. The relative loss of leavening activity during storage is virtually identical for the parental strains and the strains according to the invention. The leavening activity in high sugar doughs is not affected by the introduced modifications since the leavening activity of the novel strains transformed with integrative plasmids is as good as that obtained with the host strain.

The subject yeast host will have at least one copy of the construct, and may have two or more, usually not exceeding about 200, depending upon whether the gene is integrated into the genome, amplified, or is present on an extrachromosomal element having multiple copy numbers. Integration or non-integration may be selected, depending upon the stability required for maintenance of the extrachromosomal element prepared, the number of copies desired, the level of transcription available depending upon copy number, and the like.

The construct may include one or more structural genes with the same or different promoters. The construct may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, by synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various fragments may be combined, cloned, isolated and sequenced in accordance with conventional ways. After each manipulation, the DNA fragment or combination of fragments may be inserted into the cloning vector, the vector transformed into a cloning host, e.g. *E. coli,* the cloning host grown up, lysed, the plasmid isolated and the fragment analyzed by restriction analysis, sequencing, combinations thereof, or the like.

Various vectors may be employed during the course of development of the construct and transformation of the host cell. These vectors may include cloning vectors, expression vectors, and vectors providing for integration into the host or the use of bare DNA for transformation and integration.

The cloning vector will be characterized, for the most part, by having a replication origin functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus or the exising gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions. Of particular interest for the subject invention as the vector for expression, either for extrachromosomal stable maintenance or integration, are constructs and vectors which in their stable form in the host are free of heterologous (non-Saccharomyces) DNA.

According to a further aspect of the invention processes are provided to produce yeasts which exhibit all the advantages described above whereas in addition prokaryotic DNA sequences have been removed. This has been accomplished by gene replacement techniques (R. J. Rothstein (1983) Methods in Enzymology, 101, 202). According to the present invention these techniques are now advantageously applied to Saccharomyces cells. For example, transformation of Saccharomyces cells with a vector containing genes encoding altered maltase and/or maltose permease located in a Saccharomyces sporulation-specific gene (E. Gottlin-Ninga, D. B. Kaback (1986) Mol. Cell. Biol. 6, 2185). After introduction of this DNA into a Saccharomyces host cell homologous recombination of the newly introduced DNA takes place with the chromosomal sporulation-specific gene. As a consequence altered maltase and/or maltose permease genes embedded between the sporulation specific sequences become integrated into the chromosome. Resulting transformants are completely devoid of prokaryotic DNA.

It will be appreciated to realise that even better results may be obtained if the optimal ratio of maltase and maltose permease activity is determined. This can be done by varying the promoters of both genes or by integration of different numbers of (altered) maltase and maltose permease genes into the yeast genome, for example, by using several integration loci, according to methods as described below. The optimal ratio of maltase and maltose permease activity can also be obtained using maltase or maltose permease genes encoding other isoenzymes or maltase and maltose permease. Furthermore any enzyme can be applied, having at least maltase or maltose permease activity. In addition, genes encoding the MAL-regulatory protein can be integrated into the genome in an analogous way (see Example 1), either under control of its own, natural promoter or under control of another promoter, preferably Saccharomyces. This can also be useful in order to obtain an optimal ratio of maltase and maltose permease activity.

List of Deposited Strains

The following strains have been deposited with the CentraalBureau voor Schimmelcultures (CBS), Oosterstraat 1, Postbus 273, NL-3740 AG Baarn, Netherlands:

*Saccharomyces cerevisiae* 237 Ng (strain A) has been deposited with the CBS under the accession number 158.86 on Mar. 25, 1986;

*Saccharomyces cerevisiae* DS 15543 (strain C) has been deposited with the CBS under the accession number 406.87 on Sep. 3, 1987;

*Escherichia coli* harbouring plasmid p21–40 has been deposited with the CBS under the accession number 400.87 on Aug. 28, 1987;

*Escherichia coli* harbouring plasmid pYEF46 has been deposited with the CBS under the accession number 401.87 on Aug. 28, 1987;

*Escherichia coli* harbouring plasmid p76 has been deposited with the CBS under the accession number 402.87 on Aug. 28, 1987;

*Escherichia coli* harbouring plasmid peG418 has been deposited with the CBS under the accession number 160.86 on Mar. 25, 1986;

*Escherichia coli* harbouring plasmid pTZ19R has been deposited with the CBS under the accession number 405.87 on Sep. 3, 1987;

*Escherichia coli* harbouring plasmid pTZ329T/ADHI has been deposited with the CBS under the accession number 404.87 on Sep. 3, 1987;

*Escherichia coli* harbouring plasmid p153–215 AK has been deposited with the CBS under the accession number 403.87 on Sep. 3, 1987.

*Escherichia coli* harbouring plasmid pLF24 has been deposited with the CBS under the accession number 156.88 on Mar. 8, 1988.

*Escherichia coli* harbouring plasmid pUT332 has been deposited with the CBS under the accession number 158.88 on Mar. 8, 1988.

*Escherichia coli* harbouring plasmid pTZ18R has been deposited with the CBS under the accession number 480.88 on Jul. 27, 1988.

BRIEF DESCRIPTION OF THE DRAWINGS

FIG. 5 describes the sequence of plasmid pGb-M6g(Δ–9).
  a) maltase and maltose permease genes. Arrow indicates direction of transcription. St (StuI) served as startpoint for construction of deletion mutant. Relevant parts of sequence of intergenic area are shown below this map.
  b) Sequence of pGb-m6g (Δ –9). Deleted area extends from −9 to −417. Polylinker refers to the oligonucleotides which have been ligated onto the Ba131-treated DNA (see also FIG. 4).

FIGS. 7A–7D describe the construction of plasmid pGb-iRR01 a) plasmid pT4 is not drawn to scale. Abbreviations: E, EcoRI; B/Bg, BamHI/BglII ligation; H, HindIII
  b) mutagenesis on pT4 in order to fuse the EF1αA promoter+5'leader to the five N-terminal amino-acids codons of the maltase gene in such a way that a BglII site is created as well. Relevant sequences are shown.
  Mutagenesis primer is partly complementary (indicated with dots) to the EF1αA sequence. In the region of mismatches are the maltase codons and the -boxed- BglII recognition site (note that the presented orientation of the mutagenesis primer is 3'→5', i.e. the BglII site should be read from right to left (4'→3').
  In the maltase sequence the N-terminal five amino acid codons are indicated. The BclI recognition site is boxed
  In the sequence of pT4-M, the sequence covering the mutation is shown. BglII site is boxed. Asterisks indicate the deviation from the maltase nucleotide sequence. The deviation in the fourth codon is a silent mutation.
  c) Plasmids are not drawn to scale. Abbreviations: H, HindIII; Bc, BclI; E, EcoRI; Bg, BglII; EV, EcoRV; Bg/Bc, BglII/BclI ligation; pEF1cA (hatched box), 5' flank (promoter+5'leader sequence) of EF1cA; f1 ori, origin of replication of phage f1; amp, ampicillin resistance gene.
  d) Plasmids are not drawn to scale. Abbreviations: see c).

Figure 8:
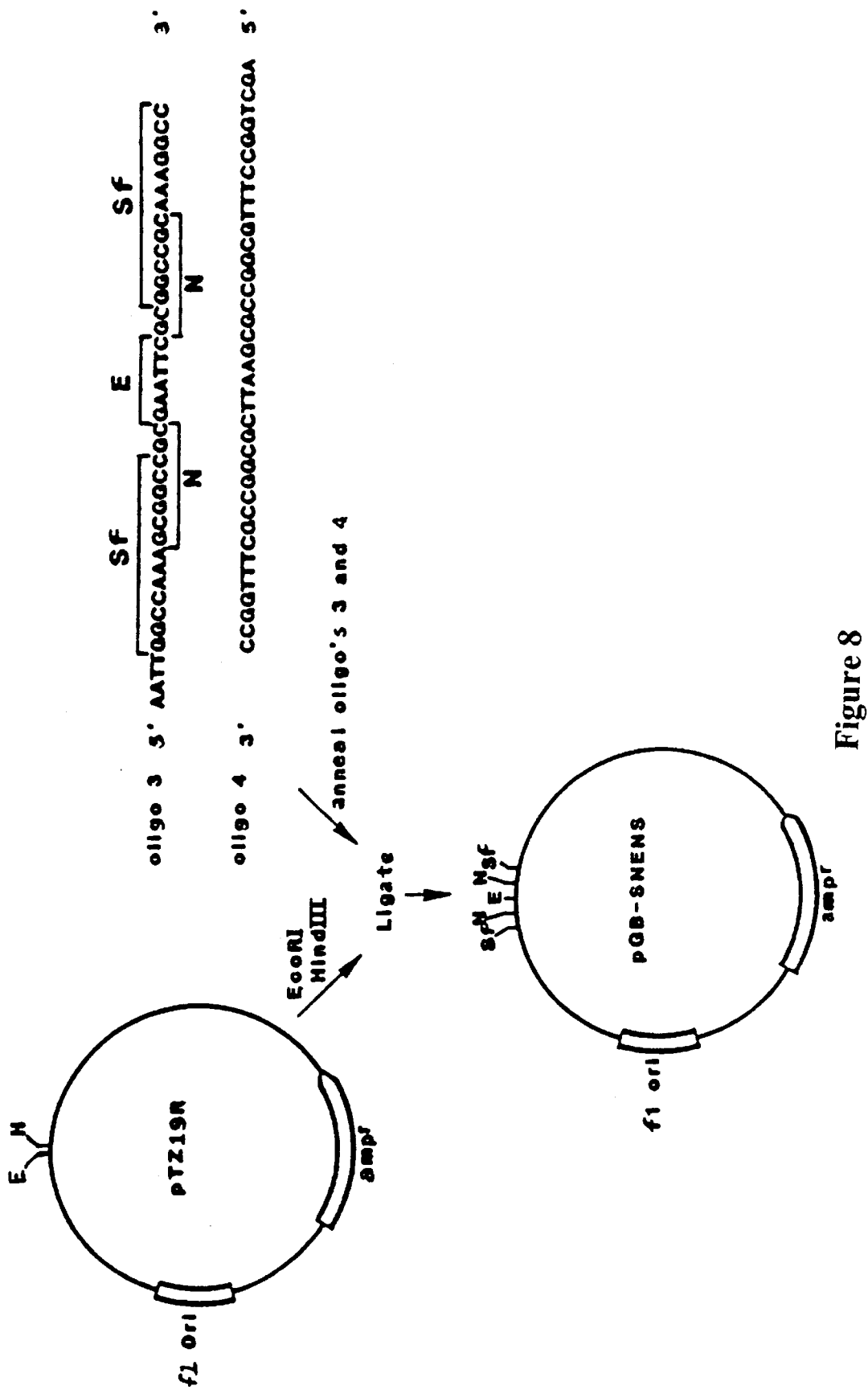

FIG. 8 describes the construction of plasmid pGB-SNENS. Plasmids are drawn schematically and not to scale. Abbreviations: E, EcoRI; H, HindIII; Sf, SfiI; N, NotI; f1 ori, origin of replication phage f1; amp. ampicillin resistance gene. Arrows indicate 5'→3' direction. Oligo 3 and 4 are synthetic oligodeoxynucleotides with the base sequence as indicated.

Figure 9:
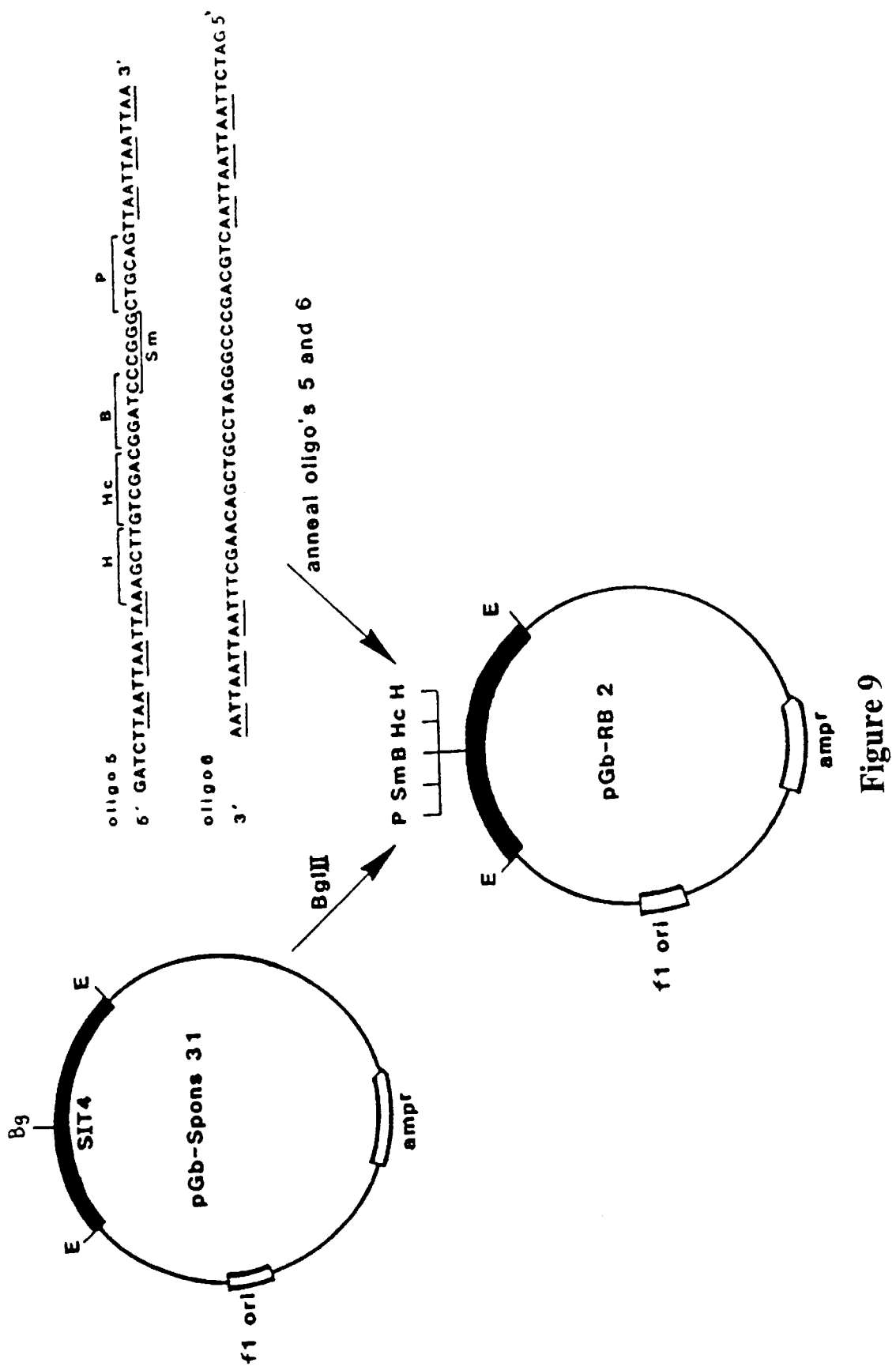

FIG. 9 describes the construction of plasmid pGb-RB2. Plasmids are drawn schematically and not to scale. Abbreviations: E, EcoRI; Bg, BglII; H, Hind III; Hc, HincII; B, Bam HI; Sm, Sma I; P, Pst I; f1 ori, origin or replication phage f1; amp, ampicillin resistance gene. Arrows indicate 5'→3' direction. Oligo 5 and 6 are synthetic oligodeoxy-nucleotides with the base sequence as indicated. Underlined are the TAA translational stopcodons in all reading frames.

Figure 10:
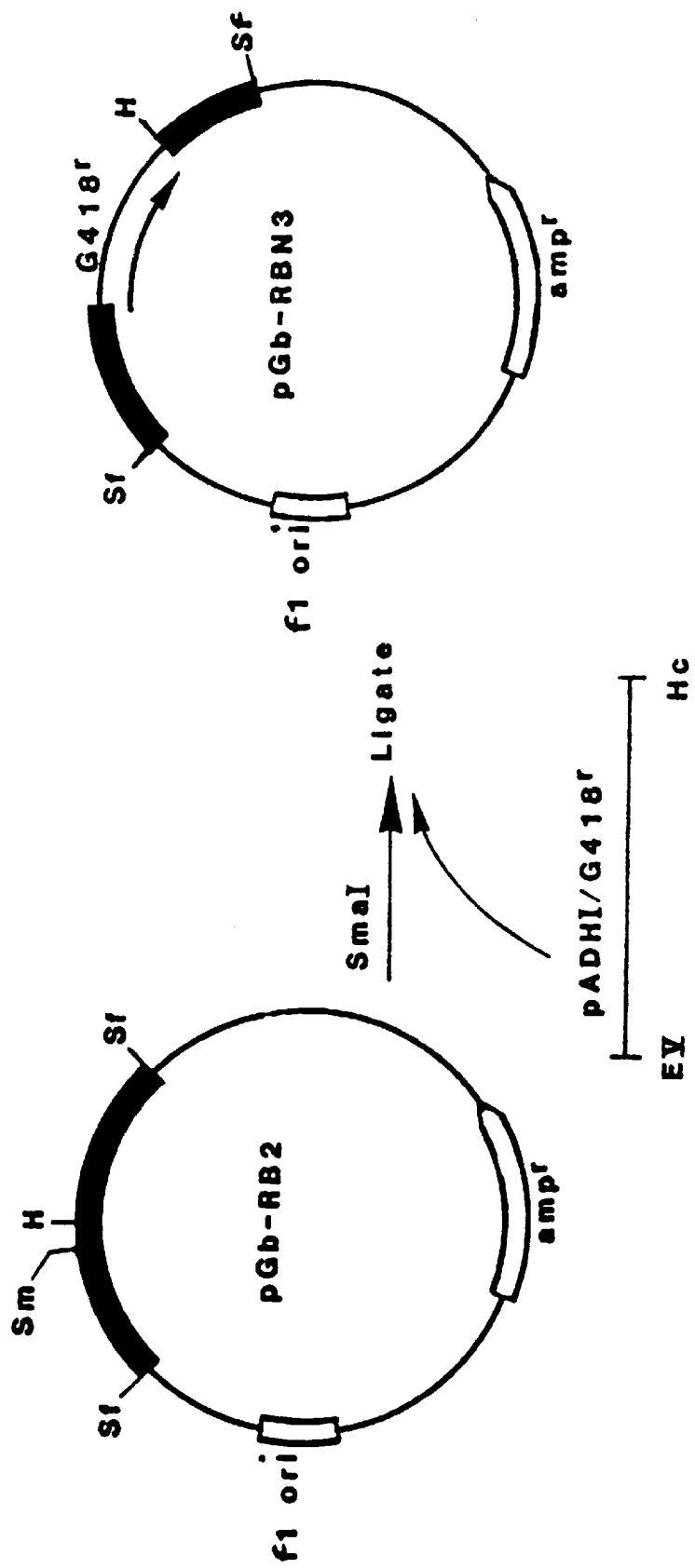

FIG. 10 describes the construction of plasmid pGb RBN 3. Arrows indicate direction of transcription. Plasmids are drawn schematically and not to scale. Abbreviations: Sf, SfiI; Sm, Sma I; H, Hind III; f1 ori, origin or replication phage f1; Amp, ampicilline resistance gene; G418, Tn5 gene (under control of ADHI promoter) conferring resistance to G418. EV, EcoRV; Hc, Hinc II.

Figure 11:
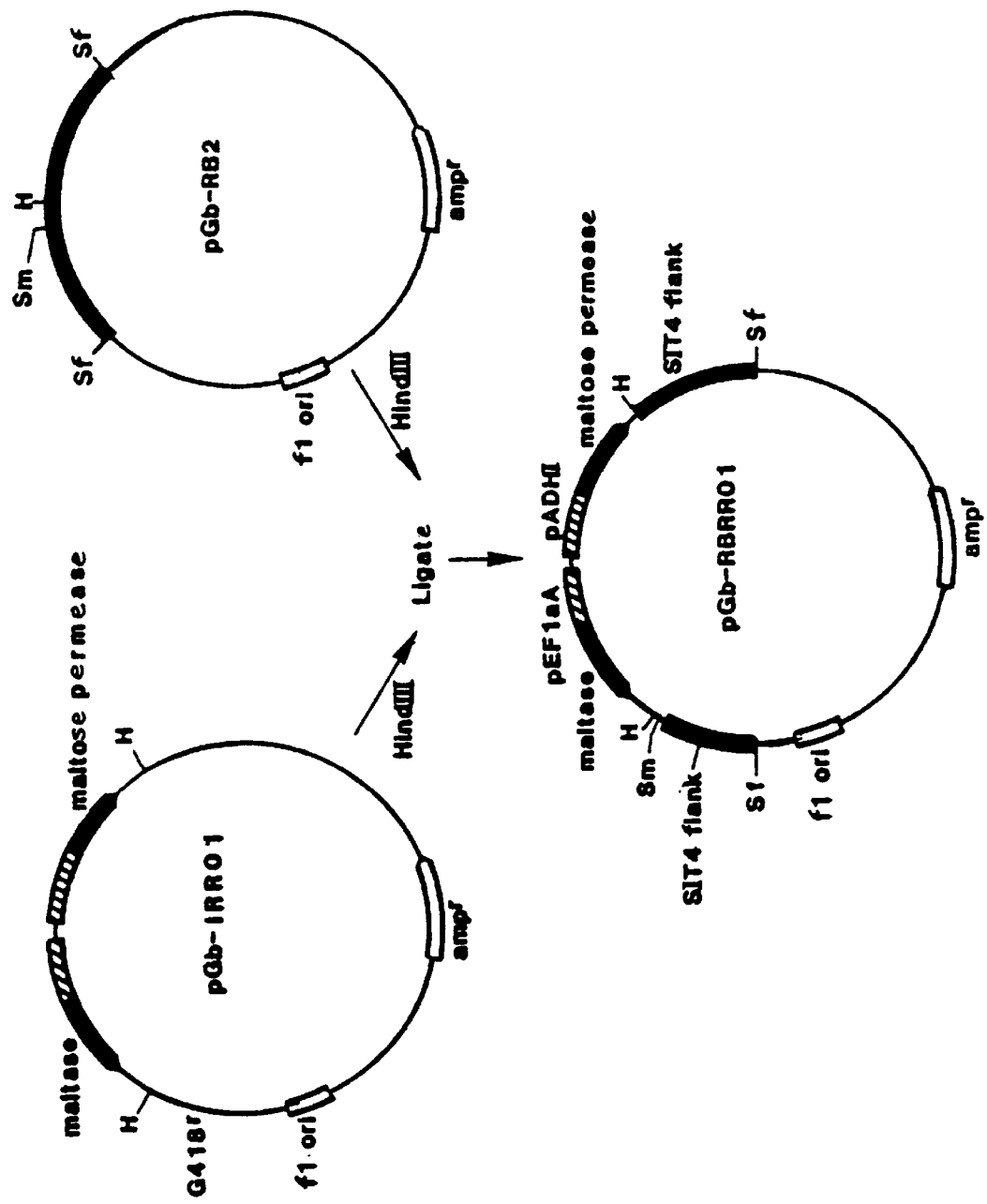

FIG. 11 describes the construction of plasmid pGb-RBRR01. Plasmid pGb-iRR01 is fully described in FIG. 7 and contains the maltase gene under direction of EF1cA promoter (pEF1cA) and the maltose permease gene under direction of the alcohol dehydrogenase I promoter (pADHI) (both promoters are indicated with hatched boxes). pGb-RB2 is described in FIG. 9. In pGb-RBRR01 the SIT4 containing fragment is divided into two parts ("SIT4flanks"). Plasmids are drawn schematically and not to scale. Abbreviations are as in legends to FIG. 10. Arrows indicate direction of transcription.

Figure 12A:
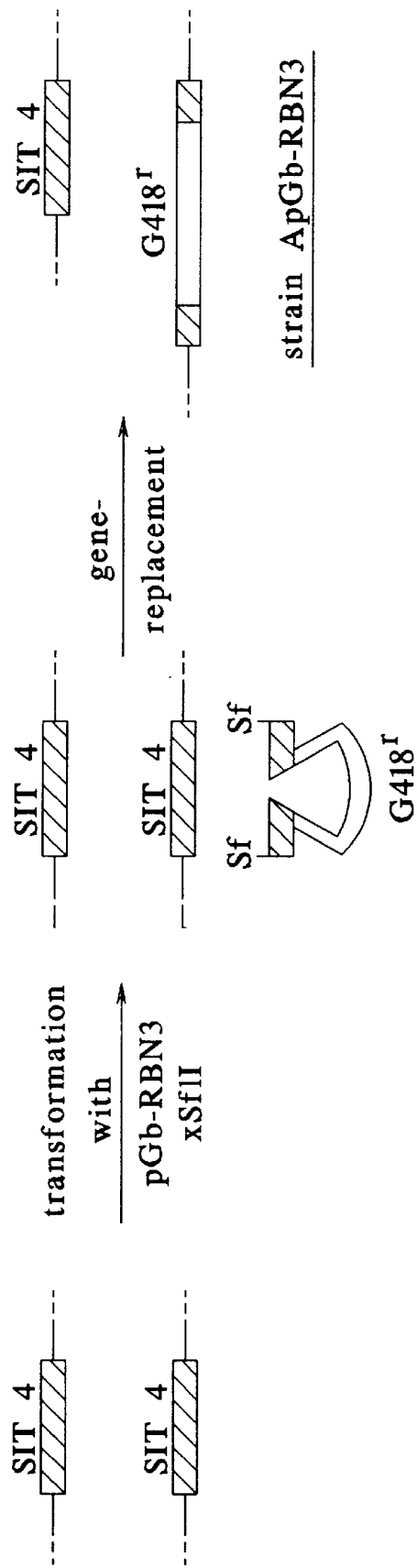
Figure 12B:
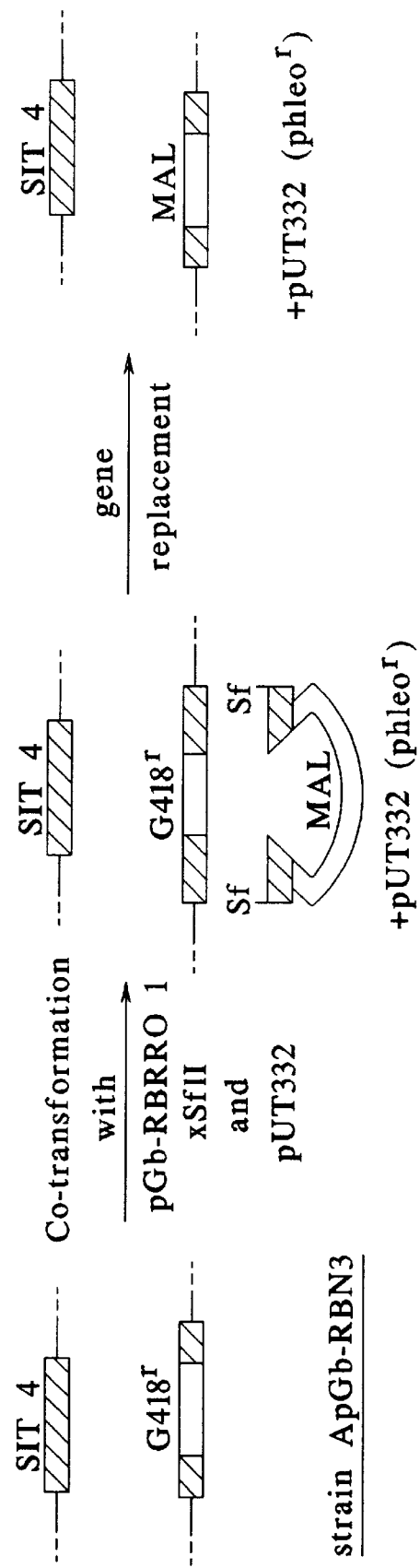
Figure 12C:
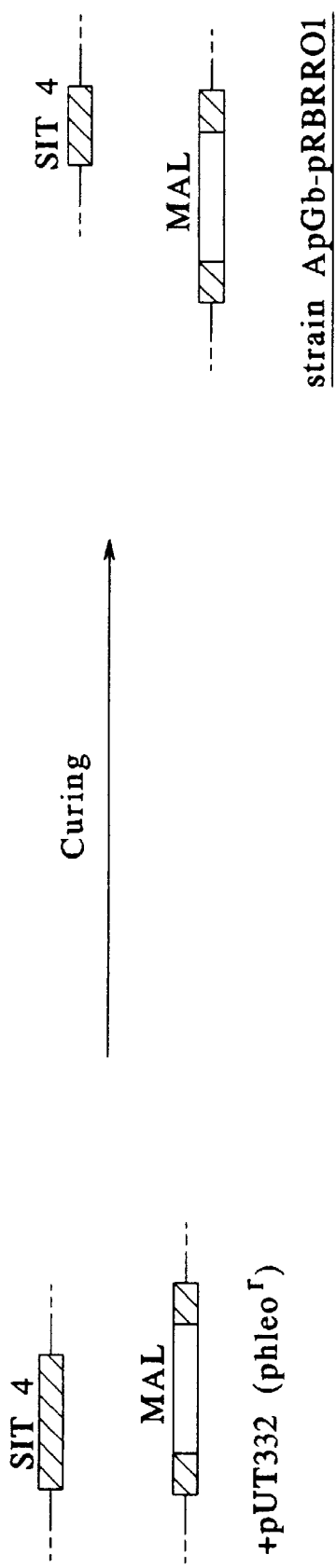

FIG. 12 describes the one-step gene disruption. In step 1, pGb-RBN3 is digested with SfiI. This liberates a DNA fragment which has on both sides homology to the SIT4 gene region. This directs integration to the SIT4 gene (see also R. J. Rothstein (1983) in Methods in Enzymology, 101, 202. The SIT4 gene region is indicated by a hatched box. Both chromosomal alleles have been shown schematically.

In step 2, the resulting strain ApGb-RBN3 is transformed with both pUT332 (undigested) and pGb-RBRR01 digested with SfiI. The principle of cotransformation is well documented (cf. A. H. Brand, I. Breeden, J. Abraham, R. Steiglanz and K. Kasmyth (1985) Cell 41, 41–48 and P. Siliciano and K. Tatchell (1984) Cell 37, 969–978) In the first selection we have used resistance against phleomycin (plasmid pUT 332) but of course 2μ-derived episomal plasmids conferring resistance to other antibiotics like hygromycin B can be used as well. PUT332 and phleomycin are commercially available from Cayla, Avenue Larrien, Centre Commercial de Gros, 31094 Toulouse Cédex, France. On pUT 332, the phleomycin-resistance gene is derived form transposon Tn5 and has been placed under the direction of a yeast promoter. In step 3 the episomal plasmid pUT332 is removed from the transformants by growth in non-selective medium (curing). Abbreviations: G418r, G418 resistance gene under direction of ADHI promoter; Sf, end of a DNA fragment generated by SfiI digestion; MAL, an altered maltase and maltose permease gene. See also FIG. 9 and 11 for details of the plasmids; +pUT332, episomal plasmid pUT332.

Figure 13:
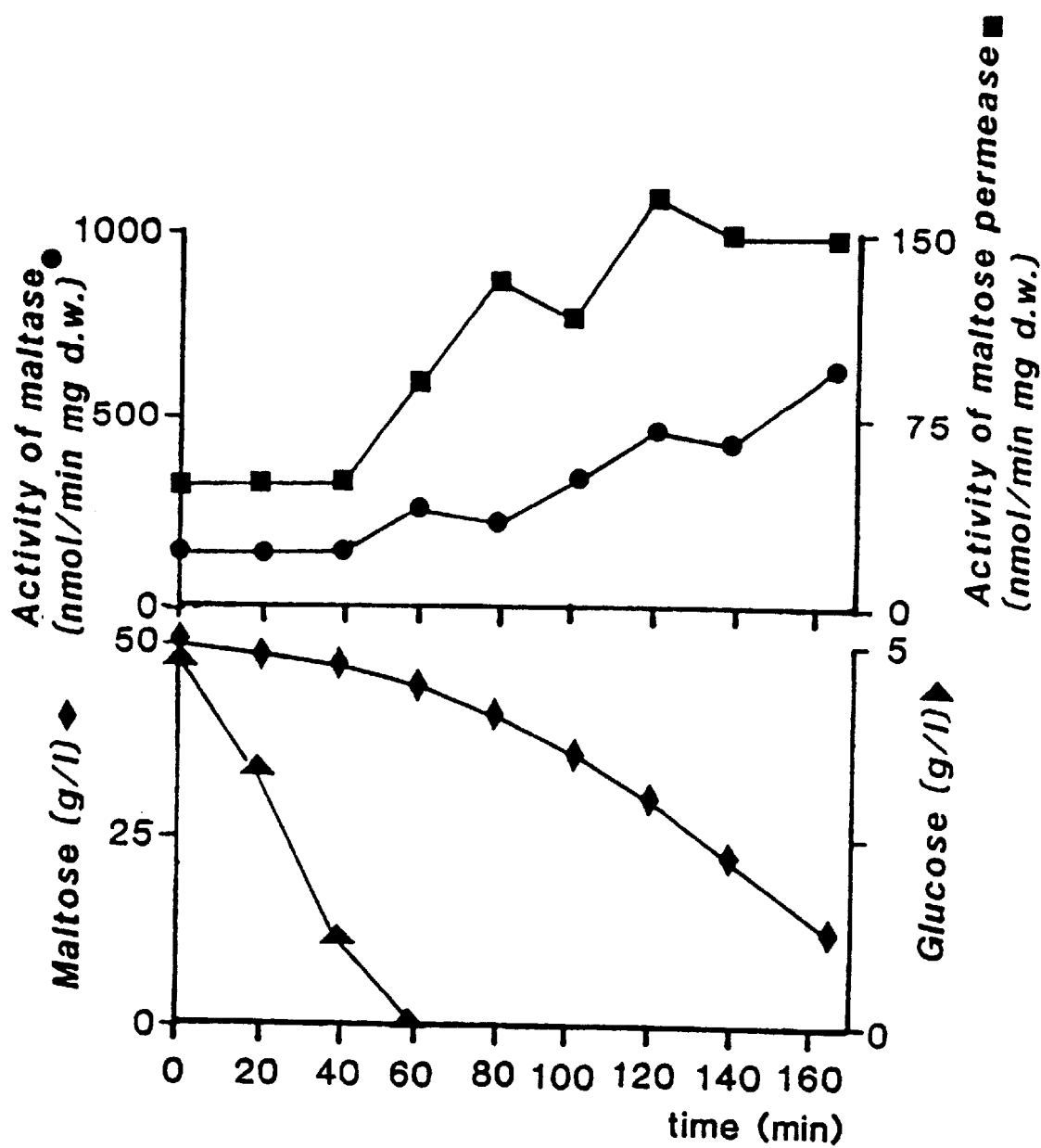

FIG. 13 describes the correlation between the increase in specific activity of maltose permease and maltase with the disappearance of glucose from medium A. Graphs are typical for commercial baker's yeast strains as for example strain A.

Figure 14:
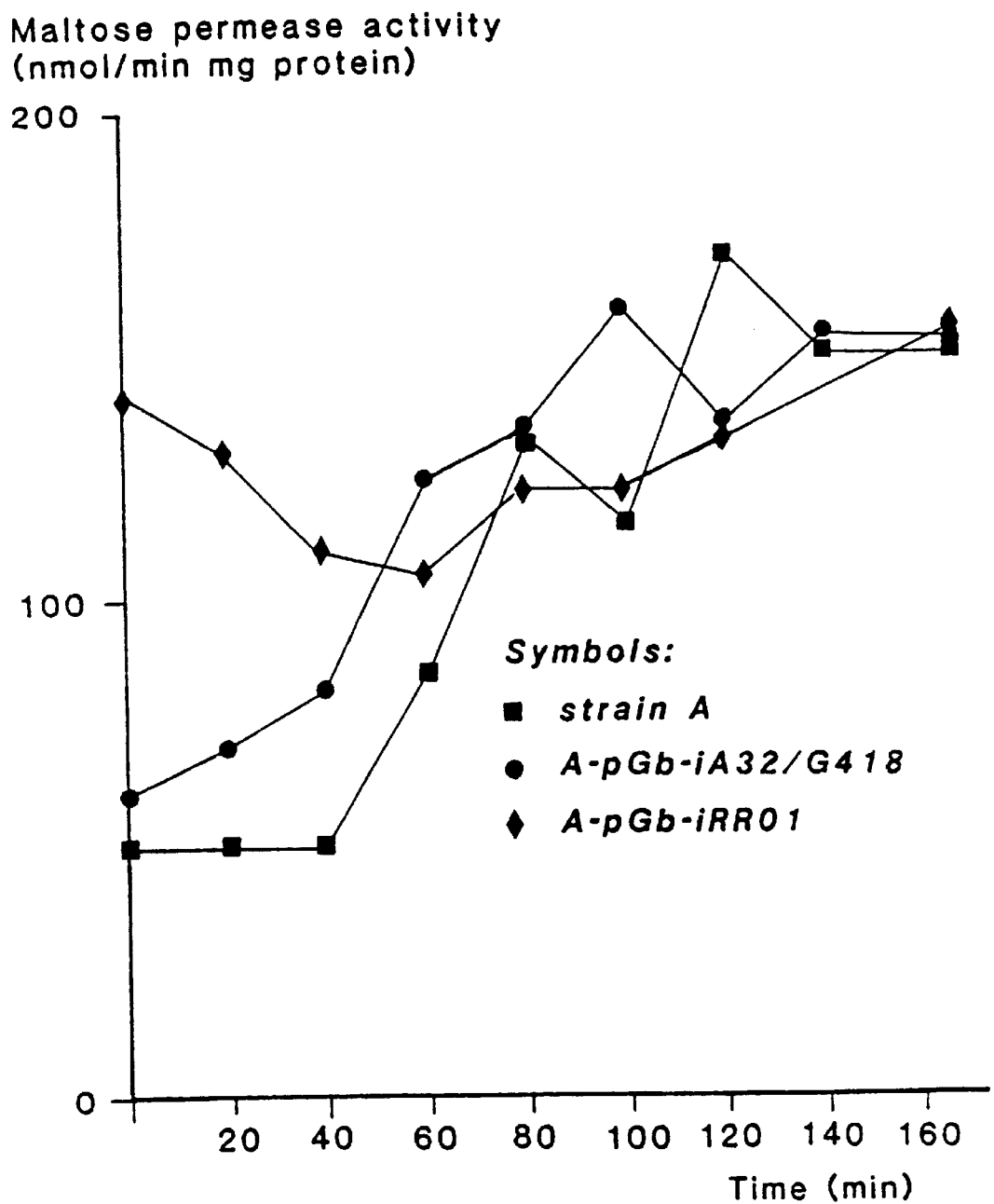

FIG. 14 describes the specific activities of maltose permease in strain A and its rDNA derivatives during a simulation of dough-rise in medium A.

Figure 15:
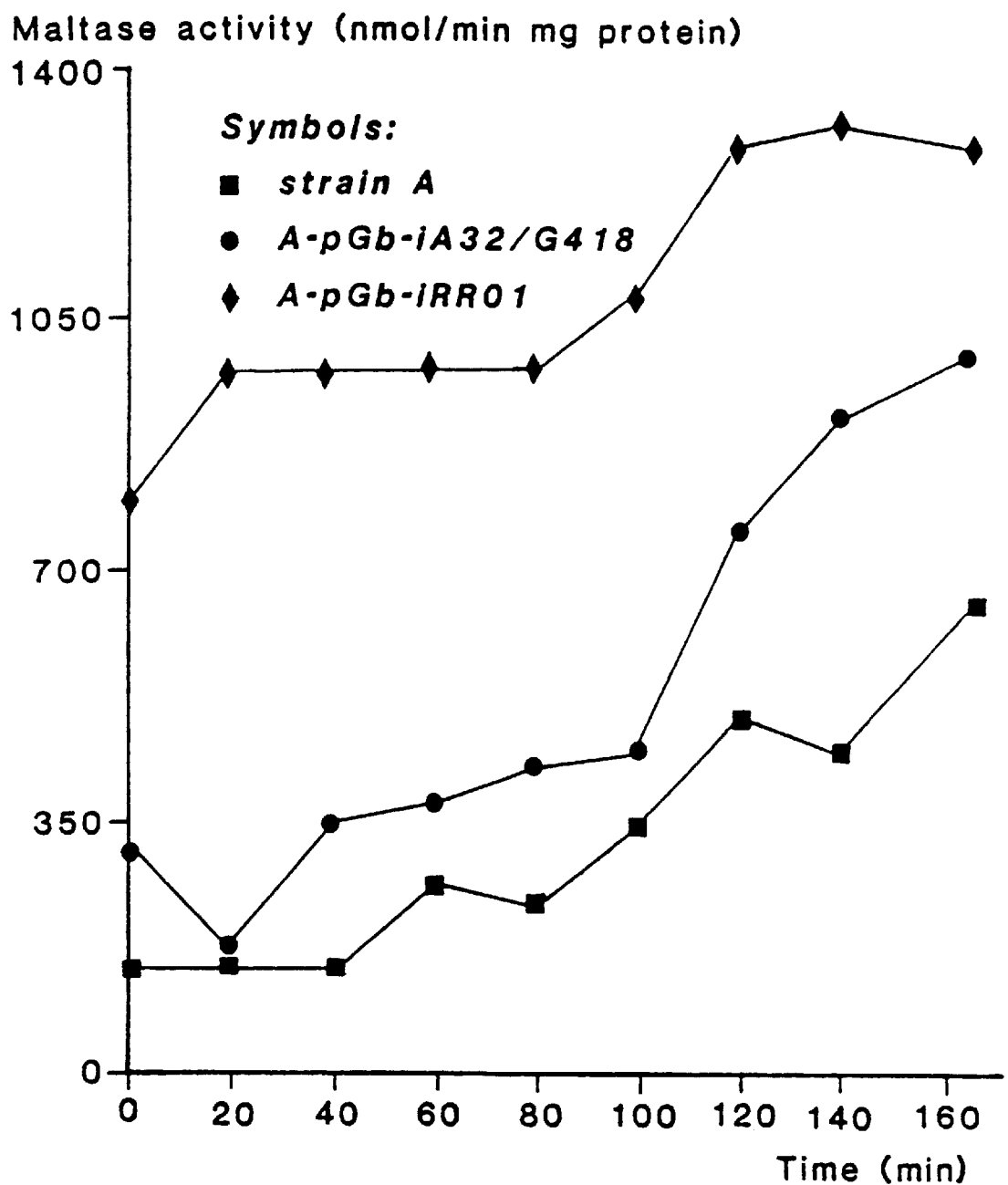

FIG. 15 describes the specific activities of maltase during a simulation of dough-rise in strain A and its rDNA derivatives in medium A containing maltose as main carbon and energy source.

Figure 16:
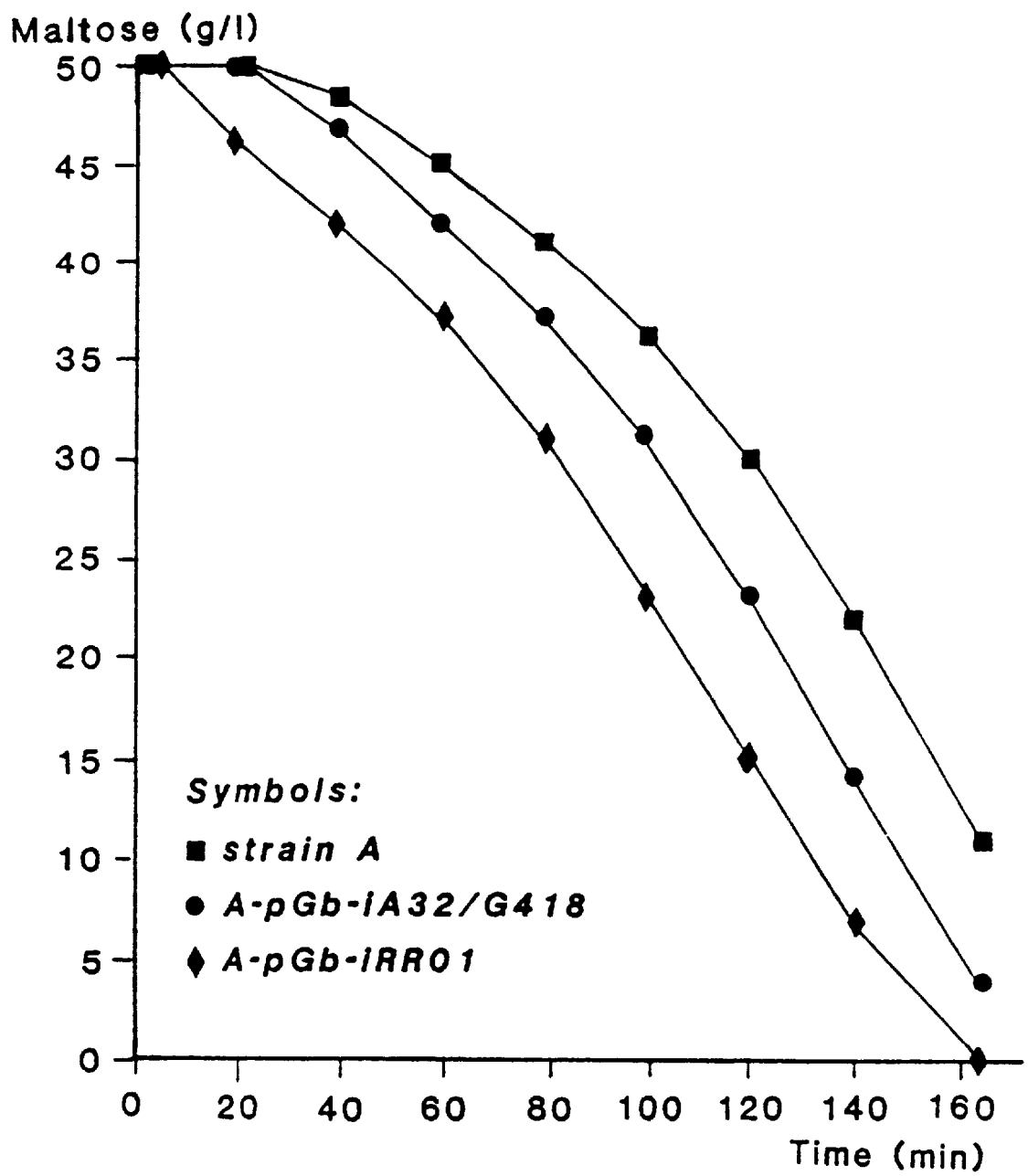

FIG. 16 describes the fermentation of maltose during a simulation of dough-rise by strain A and its rDNA derivatives in medium A containing maltose as main carbon and energy source.

Figure 17:
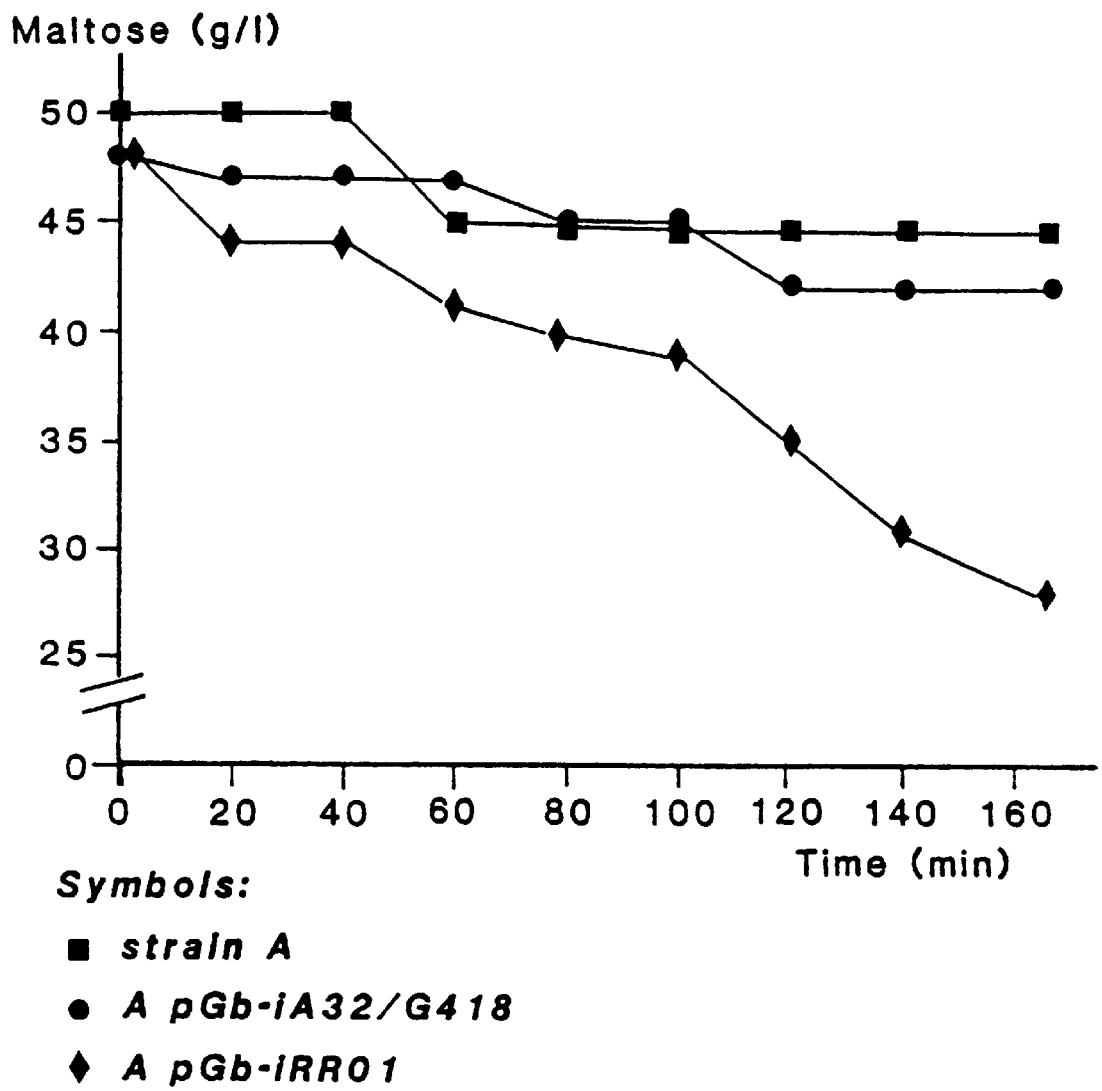

FIG. 17 describes the fermentation of maltose during a simulation of dough-rise by strain A and its rDNA derivatives in medium B containing glucose as main carbon and energy source.

The following experimental data are given to illustrate the invention. It has to be understood that a person skilled in the art who is familiar with the methods may use other yeast strains and vectors which can be equally used for the purpose of the present invention. These alterations are included in the scope of the invention.

Cloning Techniques

For general cloning techniques reference is made to the handbook of Maniatis et al. (T. Maniatis, E. P. Pritsch, J. Sambrook (1982) Molecular Clooning, A Laboratory Manual). Restriction enzymes are used as recommended by the manufacturer and are obtained either from New England Biolabs (Biolabs), Bethesda Research Laboratories (BRL) or Boehringer Mannheim (Boehringer). In general 1 to 5 units of enzyme are needed to cleave 1 μg of DNA.

Transformation of E. coli was carried out using the $CaCl_2$-technique (T. Maniatis et al., Supra).

Construction of Recombinant Plasmids 1) pGb-eMAL6g

Figure 1:
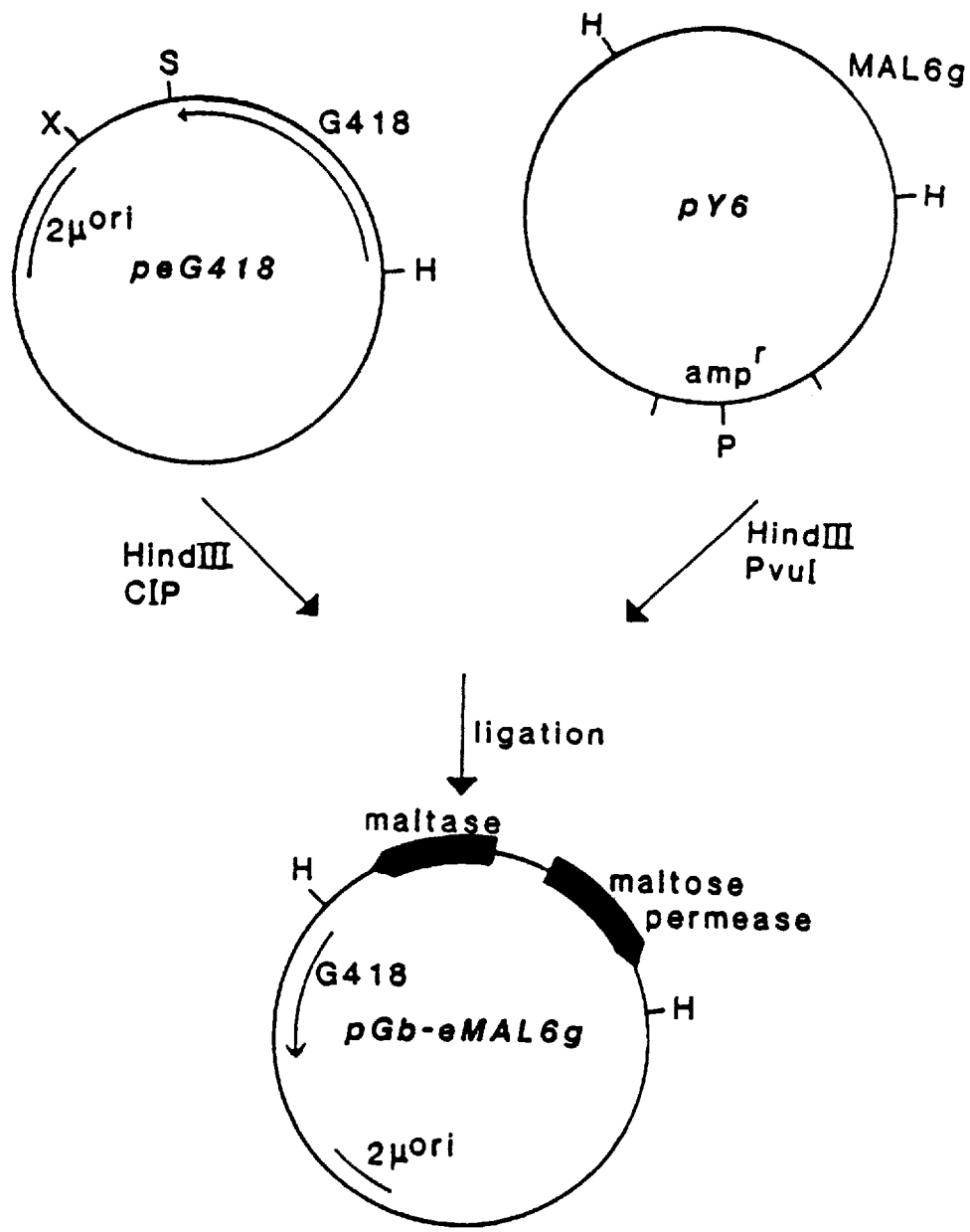
FIG. 1 describes the construction of plasmid pGb-eMAL69. Arrows indicate the direction of transcription of indicated genes. Plasmids are drawn schematically and not to scale. Abbreviations: G418, Tn5 gene (under control of ADHI promoter) conferring resistance to G418; P, PvuI; X, XbaI; S, SalI; H, HindIII; CIP; calf intestine phosphatase.

This plasmid is capable of self-replicating in yeast and contains the genes encoding maltose permease and maltase. Its construction is outlined in FIG. 1.

peG418 is derived from pEMBLYe23 (Baldari and O. Cesarini (1985), Gene 35, 27) and contains between the SalI and HindIII sites a fragment with the Tn5 gene (Reiss et al. EMBO J. (1984) 3, 3317) conferring resistance to G418 under direction of the promoter alcohol dehydrogenase I (ADHI) from yeast, similar to that as described by Bennetzen and Hall (J. C. Bennetzen and B. D. Hall (1982) J. Biol. Chem. 257, 3018). peG418 was cleaved with HindIII, dephosphorylated with CIP and ligated with a digest of pY6 ×HindIII×PvuI. pY6 is described (R. B. Needleman and C. Michels (1983) Mol. Cell. Biol. 3, 796; R. B. Needleman, D. B. Kaback, R. A. Dubin, S. L. Perkins, N. G. Rosenberg, K. A. Sutherland, D. B. Forrest, C. Michels (1984) Proc. Natl. Acad. Sci. U.S.A. 81, 2611) and contains a 7.0 kb HindIII fragment comprising the MAL6 locus. This yielded pGb-eMal6g.

2. pGb-eMAL61

Figure 2:
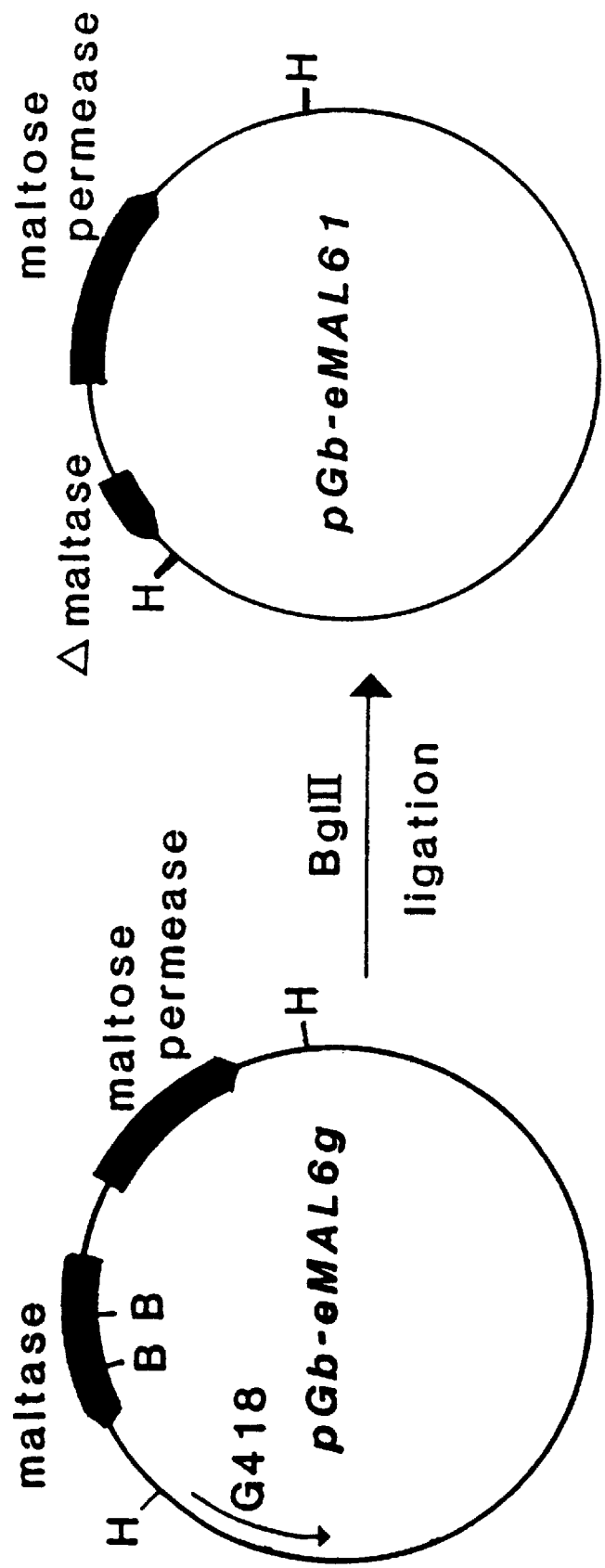
FIG. 2 describes the construction of pGb-eMAL61. Plasmids are drawn schematically and not to scale. Abbreviations: Δ maltase partial deletion maltase gene; B, BglIII. See also description of FIG. 1.

This 2μ-derived episomal plasmid contains the gene encoding maltose permease. Its construction is outlined in FIG. 2.

pGb-eMAL6g contains two BglII sites, both lying in the maltose gene. This 1.4 kb BglII has been deleted from pGb-eMAL6g by digestion with BglII, followed by dilute religation to promote intramolecular ligation. Such a deletion has been shown to destroy maltase function (J. D. Cohen, J. J. Goldenthal, T. Chow, B. Buchferer and J. Marmur (1985) Mol. Gen. Genet. 20, 1).

3. pGb-eMAL63

This 2μ-derived episomal plasmid contains DNA covering the MALp function (regulatory protein gene or MAL-regulator). Its construction is outlined in FIG. 3.

From p21-40 (R. B. Needleman and C. Michels (1983), Supra) the KpnI-SalI fragment was isolated containing the regulatory protein gene. This fragment was made blunt-ended using T4 DNA polymerase and the Klenow-DNA polymerase and thereafter cloned into the filled-in HindIII site of peG418.

4. pGb-H6g(Δ-9)

Figure 4:
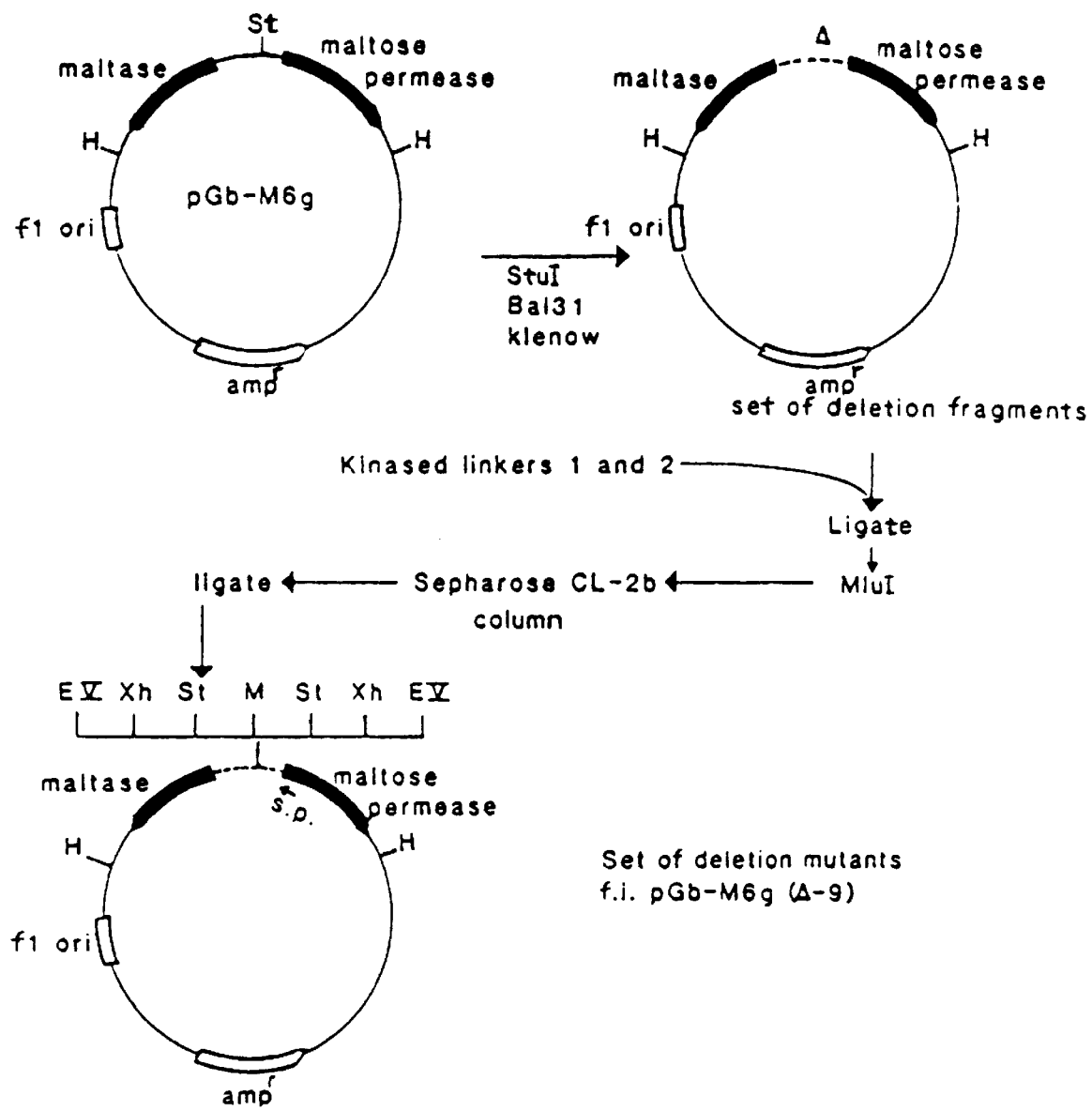
FIG. 4 describes the construction of pGb-M6g(Δ–9). Abbreviations: H, Hind III; St, StuI; Klenow, large fragment DNA polymerase I; EV, EcoRV; Xh, XhOI; M, MluI; f1 ori, origin of replication phage f1; amp, ampicillin resistance gene; s.p. sequence primer. Arrows indicate 5'→3'direction. Deleted area is indicated with dotted lines and Δ.

This plasmid is a promoter-deletion mutant made in the intergenic region of the divergently transcribed genes maltose permease and maltase (see FIG. 4). This region contains the promoters for both genes (S. H. Hong and J. Marmur (1986) Gene 41, 75). This deletion mutant has been made in order to replace the original promoters. The construction comprises the following steps:

a) The approximately 7.0 kp HindIII fragment containing the genes for maltase and maltose permease (see also FIG. 1) was cloned into the HindIII site of pTZ19R. This plasmid is commercially available (Pharmacia). This results in pGb-M6g.

b) pGb-M6g was linearized with StuI, which cuts in the intergenic region. This StuI-generated ends served as starting point for the exonuclease Bal31 in order to nibble off (parts of) the promoters-containing intergenic area. StuI lies closer to the maltose permease gene (S. H. Hong and J. Marmur (1986), Supra). the Bal31 incubation was carried out as described by Maniatis et al (T. Maniatis, E. P. Fritsch and J. Sambrook (1982), Supra). At appropriate times sampler have been removed from the reaction and incubated with Klenow DNA polymerase to make blunt-ends. Then synthetic linkers have been ligated onto the ends containing several restriction sites.

The following complementary oligodeoxynucleotides have been used:

1. 5' GATATC CTCGAG AGGCT A 3'
2. 3' CTATAG GAGCTC TCCGGA TGCGC 5'

In double-strand form restriction sites are created for EcoRV (GATATC), XHoI (CTCGAG), StuI (AGGCCT), ligation at the sticky end creates a MluI site (ACGCGT). After kinase-reaction, the linkers have been ligated onto the Bal31 treated DNA, according to conditions as described (T. Maniatis et al., (1982) Supra). The reaction mixture was then incubated with MluI and chromatographed through a 5 ml Sepharose Cl-2B column in order to separate the non-ligated oligodeoxynucleotides from the DNA fragment. Fractions containing this linear DNA were pooled, ligated to plasmid DNA and introduced into bacteria.

c) The resulting set of deletion mutants were subjected to sequence analysis. To this end, the double-stranded plasmids were converted into single-stranded DNA by superinfection with a helper phage (protocol according to recommendation of supplier). The single-stranded templated were extracted by normal M13 procedures for use in dideoxysequencing (F. Sanger, S. Nicklen and A. R. Coulson (1977) Proc. Natl. Acad. Sci. 74, 5463). As a primer we have used a synthetic oligodeoxynucleotide (5'-GAATTCGGTAGCCTTCACGC-3'), complementary to a stretch of DNA near the ATG startcondon of the maltose permease gene. Its orientation is such that the sequence is read towards the promoter (see also FIG. 4).

The deletion mutant in which most of the maltose permease promoter had been removed, was selected for further experiments. (Part of) the maltose promoter is still present (note that the StuI site as startpoint for exonuclease treatment is located asymmetrically in the intergenic region). FIG. 5 lists the sequence at the deletion point of the mutant pGb-H6g($\Delta$-9). this is compared to the recently determined sequence of this entire area (S. H. Hong and J. Marmur (1986) Supra). In the wild type sequence, one difference has been observed with the published sequence: the C at -878 (numbering according to S. H. Hong and J. Marmur (1986) Supra) is not present in our sequence. In accordance, the DNA cannot be digested with HpaI or HincII at this position.

Plasmid pGb-MBg($\Delta$-9) is the starting plasmid to fuse other promoters to both the maltose permease gene and the maltase gene (see below).

5. pGb-iA32/G418

Figure 6A:
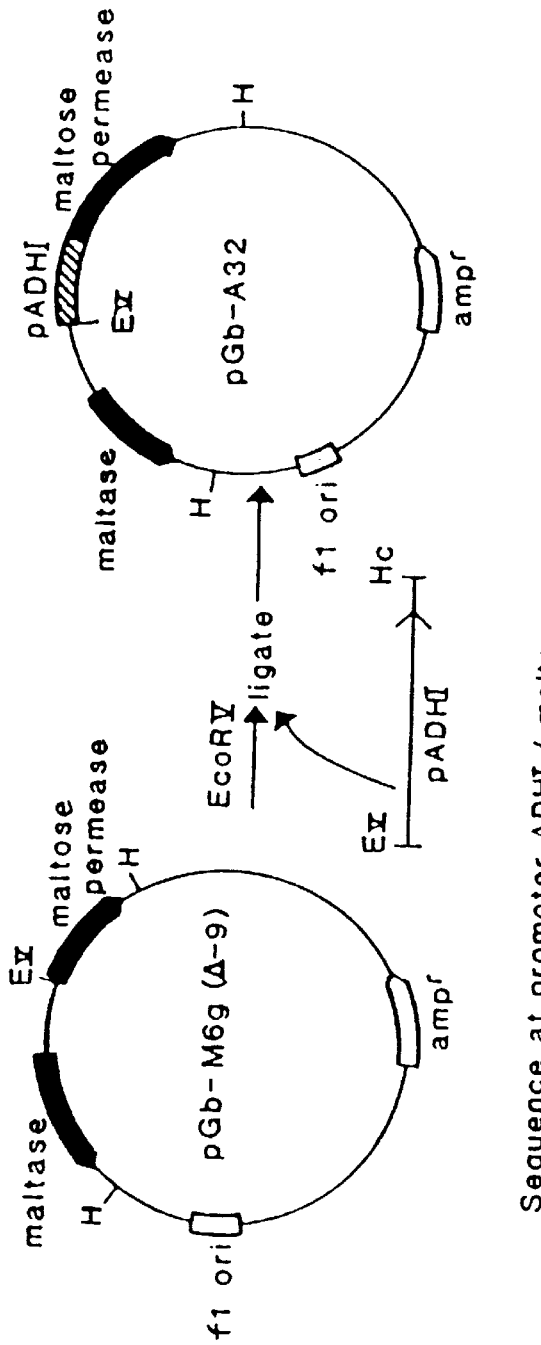
FIGS. 6A–6B describe the construction of plasmid pGb-iA32/0418. Arrows indicate direction of transcription. Plasmids are drawn schematically and not to scale. Abbreviations: H, Hind III; EV, EcoRV; f1 ori, origin of replication phage f1; amp, ampicillin resistance gene; G418, Tn5 gene (ADHI promoter) conferring resistance to G418; S, SmaI; Hc, HincII; pADHI, promoter alcohol dehydrogenase I gene+part 5' leader (hatched area).
Figure 6B:
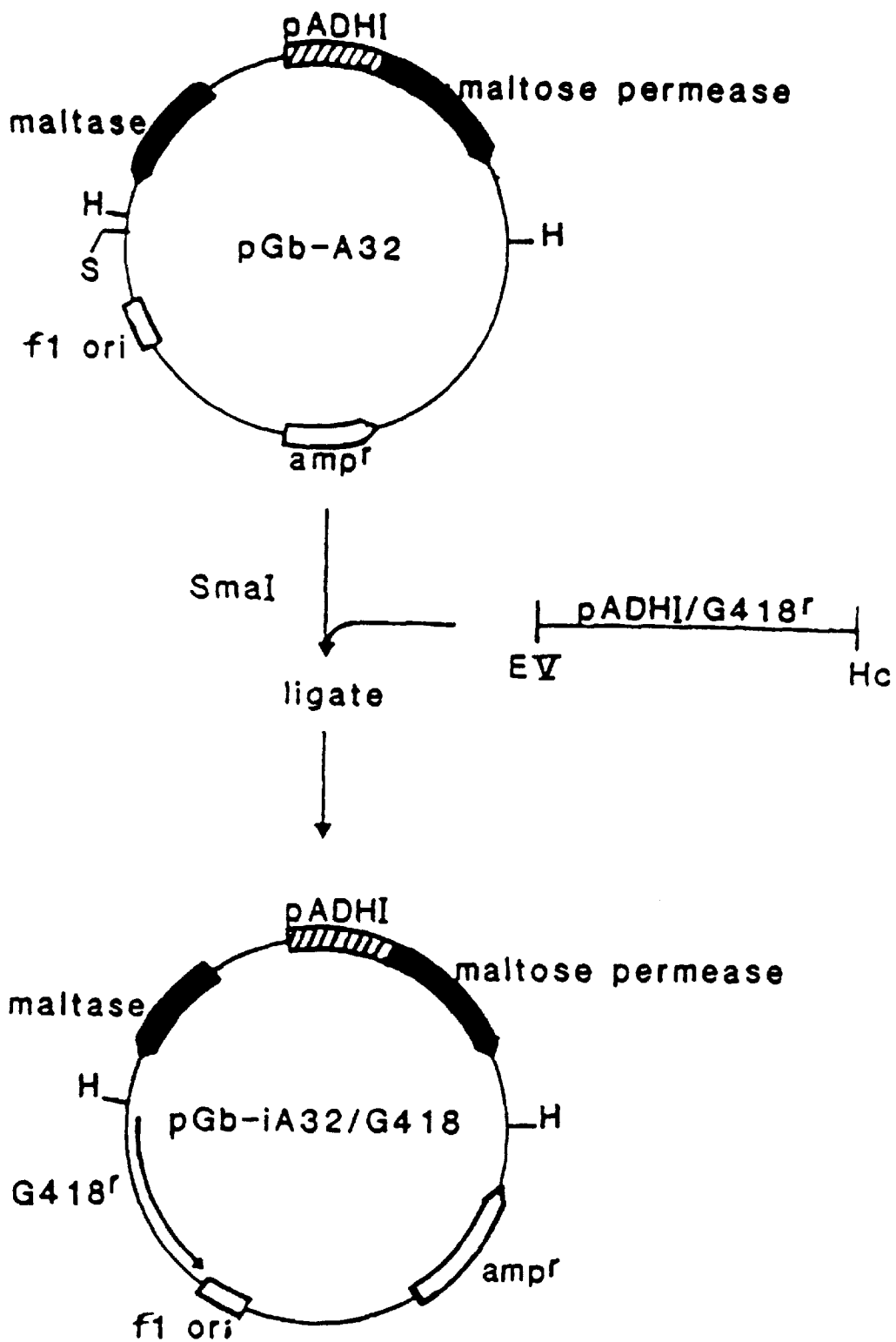
Figure 7A:
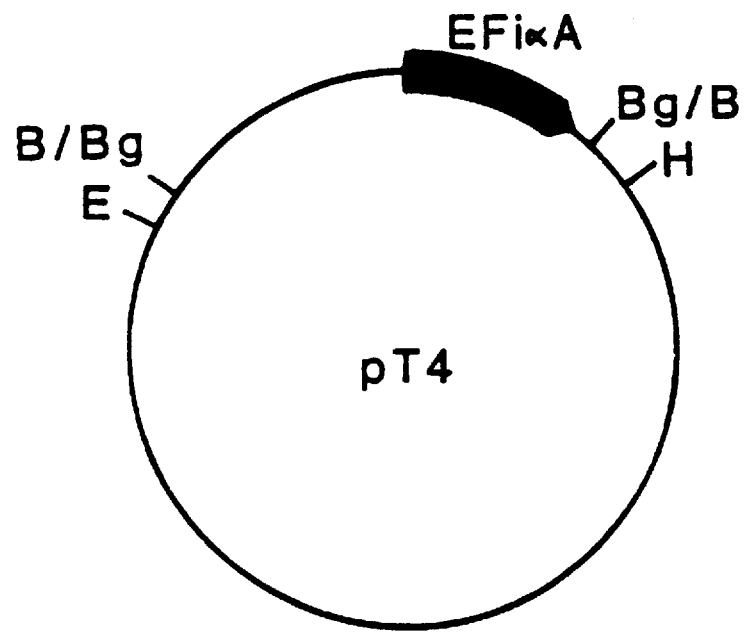
Figure 7B:
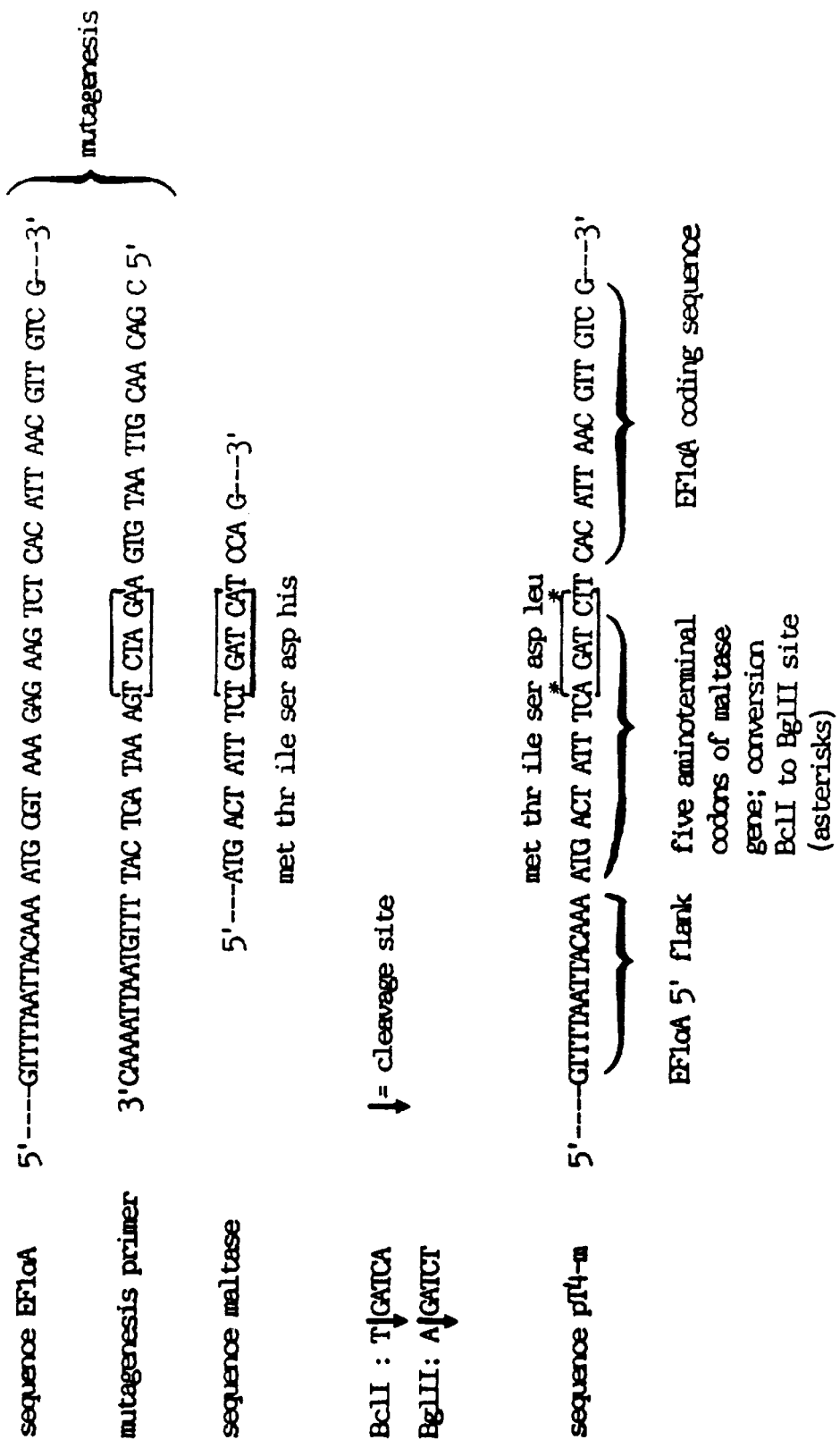
Figure 7C:
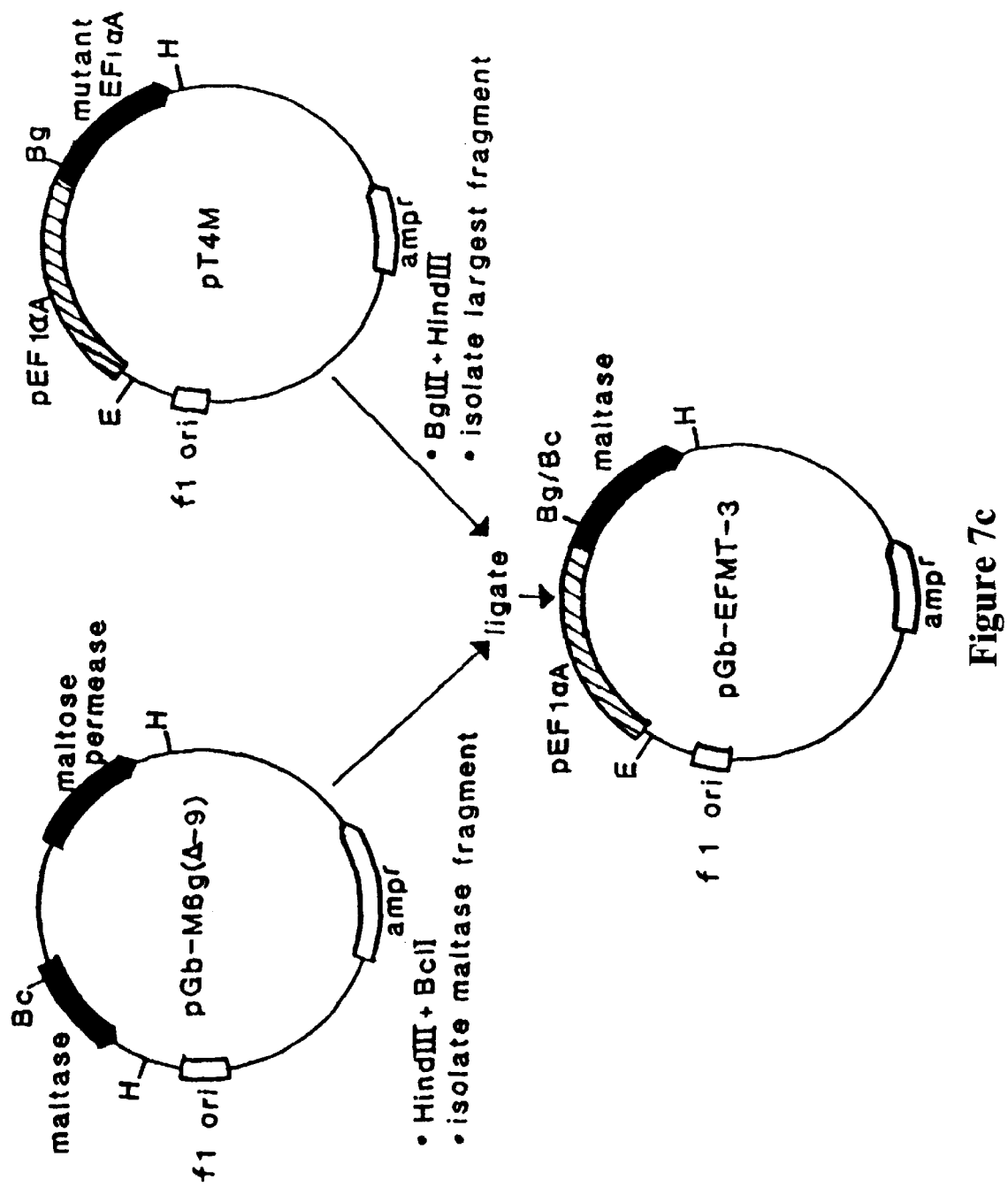
Figure 7D:
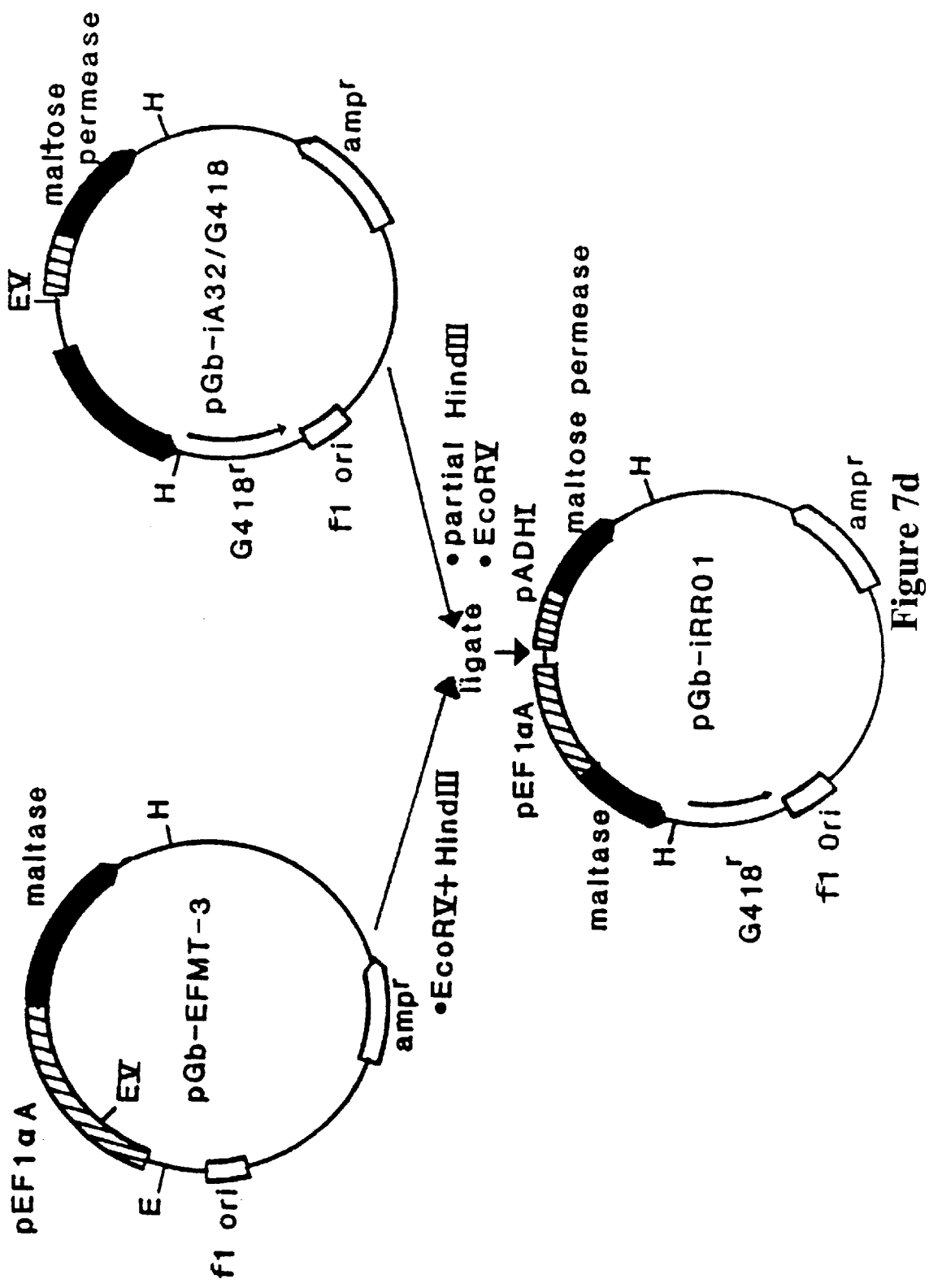

This plasmid is an integrating yeast plasmid. It contains the maltose permease gene, hooked onto the alcohol dehydrogenase I promoter and part of its 5' leader sequence. Its construction was as follows (FIG. 6).

a) Plasmid pTZ19R/ADHI contains a 1.4 kb BamHI fragment with the ADHI promoter, starting at position -15 relative to the AUG codon (J. L. Bennetten and B. D. Hall (1982) J. Biol. Chem. 257, 3018). From this plasmid, the 700 bp EcoRV-HincII fragment has been isolated and ligated to EcoRV digested pGb-M6g ($\Delta$-9). Resulting plasmids were analyzed with restriction enzyme digestions and the proper orientation was confirmed via dideoxy sequence analysis on single-stranded templates (see FIG. 6). The same oligoprimer was used to described in section 4c.

As a result of the cloning procedure of the ADHI promoter fragment, part of the polylinker of pTZ19R (BamHI-HincII) is present between the maltose permease gene and the ADHI promoter. Structure and sequence of pGb-A32 is shown in FIG. 6a.

b) Plasmid pGb-A32 was provided with the dominant selection marker G418$^{res}$. A 1.9 kp EcoRV/HincII fragment contains the Tn5 gene conferring resistance to G418 under direction of the promoter alcohol dehydrogenase I. This fragment was isolated by an EcoRV/HincII double digestion of plasmid 153–215 Ak. The EcoRV/HincII fragment was cloned into the SmaI site of pGb-A32. This yielded pGb-iA32/G418.

6. pGb-iRRol

This plasmid is an integrating plasmid. It contains the maltose permease gene under direction of the promoter alcohol dehydrogenase I and the maltase gene under direction of the promoter translation elongated factor EP1$\alpha$A. The cloning pathway is depicted in FIG. 7. The approach was as follows: The maltase gene contains a BclI site around the fifth amino acid codon. Therefore the EP1$\alpha$A coding region was mutagenized in such a way that the first five amino acids became identical to those of the maltase protein. A BglII site was co-introduced at the position of the BclI site. Conversion of a BclI site to a BglII site is a silent mutation in the fourth codon. Via a BglII/BclI ligation the EP1$\alpha$A promoter and leader sequence could be fused to the rest of the maltase gene. The procedure comprised the following steps:

a) The starting plasmid was pYEP46 (S. Nagata, K. Nagashima, Y. Tsunetsugu-Tokota, K. Fuyimura, M. Miyaraki and Y. Kaziro (1964) EMBO J. 3, 1962) which contains the entire gene coding for EP1$\alpha$A. A 2.5 kb BglII fragment covering this gene, was isolated and cloned into the BamHI site of pTZ19R. Clone pT4 was picked up (see FIG. 7a) and used for the oligodeoxynucleotide directed mutagenesis.

b) After superinfection with helper phage, single stranded (ss) DNA of pT4 was isolated. 400 ng as DNA, 400 ng heat-denatured pTZ19RxBamHI and 100 ng mutagenesis oligodeoxynucleotide (see FIG. 7b) were incubated in a volume of 10 $\mu$l of 7 nN Tris HCl pH 7.5; 50 mM Nal and 7 mM MgCl$_2$ for 10 minutes at 56° C. After 10 minutes at room temperature, second strand synthesis and ligation were started by addition of 1 $\mu$l of Klenox DNA polymerase (2U). 1 $\mu$l of T4 DNA ligase (4U), 1 $\mu$l TMD (200 mM Tris HCl pH 7.5, 100 mM MgCl$_2$, 100 mM DTT), 4 $\mu$l 2.5 mM dNTP-mix, 1 $\mu$l 10 mM ATP and 2 $\mu$l H$_2$O. End-volume was 20 $\mu$l, incubation was performed for 16 hours at 17° C. after which the mixture was transformed to E. coli JM101. Mutants were screened by colony hybridization with a kinased oligodeoxynucleotide, specific for the mutant (see FIG. 7b). This screening oligomer 5'-GACTATTTCAGATCTTC-3' was complementary to the introduced maltase codons and flanking nucleotides. The hybridization was carried out for 16 hours in 6×NET (1×NET=0.15M NaCl, 0.015M Tris HCl pH 7.5, 0.001M EDTA) at 25° C. Post hybridization washes were performed in the same mix at the same temperature (3 times 10 minutes), followed by a wash in 3×NET at 25° C. Several positive colonies was analysed further. BglII, digestion confirmed the presence of a BglII site. In addition, single-stranded DNA was isolated from a BglII-site containing mutant (pT4-M) and subjected to dideoxy sequence analysis using a synthetic 17-mer primer, complementary to nucleotides 87–103 of the EP1$\alpha$A gene (S. Nagata, K. Nagashima, Y. Tsunetsugu-Yokota, K. Fuyimura, M. Miyaraki and Y. Kaziro (1984) EMBO J. 3, 1825) (5'-CAATACCACCACACTTG-3'). The sequence obtained confirmed the successful introduction of the desired mutations.

c) The next step was to isolate the EF1$\alpha$A promoter/NH$_2$-terminal maltase gene segment from pT4-M and to fuse it via BglII/BclI sticky end ligation to the rest of the maltase gene. This step restores and maltase coding region downstream of the EP1$\alpha$A promoter and leader sequence (see FIG. 7c). Plasmid pGb-M6g ($\Delta$-9) was transformed to BM113, an E. coli dam strain, in order to be able to use the BclI site (which is methylation sensitive) (GM113: thr$^-$, leuB6, proA2, tris-4, metB1, lacY1, galK2, ara-14, tax33, thi-1, thyA12, decB16, supE44, rpaL260, dam$^-$3). A 3.8 kb BclI/HindIII fragment was isolated, containing the maltase gene except for the very NH$_2$-terminal end. pT4-M was digested with BglII/HindIII and the large 4.1 kb fragment isolated (EF1αA promoter/NH$_2$ terminal and maltase gene). Both fragments were ligated to each other, resulting in pGb-EFMT-3. Sequence analysis confirmed the correctness of all introduced mutations.

d) Finally, pGb-EFMT-3 was digested with EcoRV and HindIII to purify a 4.8 kbp. EF1αA/maltase promoter/gene fragment. From pGb-iA32/G418 (see FIG. 6). an approximately 8.3 kg HindIII (partial)/EcoRV fragment was isolated. This consists of the pTZ19R backbone, the ADHI/maltase permease promoter/gene segment and the ADHI/G418$^{res}$ segments. Both were ligated to yield pGb-iRRo1 (see FIG. 7*d*).

7. pGb-RB2

This plasmid serves as cloning vehicle to integrate pieces of DNA into the SIT4 gene of *Saccharomyces cerevisiae*. Its construction comprises the following steps (see FIGS. 8 and 9).

a. pTZ19R was digested with EcoRI and HindIII to replace its polylinker by a synthetically made DNA segment of 40 nucleotides. This piece of DNA is made by annealing of the synthetic oligodexoynucleotides 3 and 4 (see FIG. 8). This short fragment contains EcoRI and HindIII sticky ends. Cloning of this DNA fragment into the pTZ19R vector does not restore the EcoRI and HindIII sites. The synthetic DNA fragment contains at the borders restriction sites for NotI and SfiI and in the middle an EcoRI site, as indicated. The resulting plasmid is designated pGb-SNENS.

b. An EcoRI fragment containing the SIT4 gene (Gottlin-Ninga and Kaback, vide supra) was isolated from pLF24 (also known having the code pLN420) and cloned into the EcoRI site of pGb-SNENS. This yielded pGb-Spons31. Due to lack of useful reference restriction sites, its orientation it unknown.

c. Plasmid pGb-Sons 31 contains a unique GblII site in the middle of the SIT4 gene. This can be used as site into which any segment of DNA to be transferred to the SIT4 gene by gene replacement, can be cloned. To facilitate cloning manipulation, the SIT4 gene has been provided with a synthetic piece of DNA, containing several unique restriction sites. The construction of pGb-RB2 is outlined in FIG. 9.

The synthetic DNA fragment has two sticky BglII ends. Its orientation in pGb-RB2, as indicated in FIG. 9, is based on restriction enzyme analysis of pGb-RBN3 (see next).

8. pGb-RBN3

A 1.9 kb EcoRV/HincII fragment containing the G416$^{res}$ gene under control of the ADHI promoter (see also construction of pGb-iA32/G418), was cloned into the SmaI site of pGb-R52. This yielded pGb-RBN3 (FIG. 10).

9. pGb-RBRR01

This plasmid contains the maltose permease gene under direction of the promoter alcohol dehydrogenase I and the maltase gene under direction of the EF1αA promoter. Both are located on an 8.3 kb HindIII fragment which has been cloned into the SIT4 gene. Its construction is outlined in FIG. 11. To this end, pGb-iRR01 was digested with HindIII and ligated onto pGb-RB2 xHindIII (treated with calf intestine phosphatase). This yielded pGb-RBRR01.

10. pGb-RBREG01

This plasmid contains the MAL-regulator gene under direction of the promoter alcohol dehydrogenase.

I. pGb-RBREG01 can be constructed as follows. From p21-40 (R. B. Needleman and C. Michels (1983), supra) the SalI fragment is isolated containing the regulatory protein gene. This fragment is cloned into the SalI site of pTZ18R. This plasmid is commercially available (Pharmacia). Its orientation is such that the promoter area of the MAL-regulator gene is proximal to the T7-promoter sequence of pTZ18R. Using the sequence-primer of PTZ18R and other newly made oligonucleotide primers based on the DNA sequence obtained, the promoter area of the MAL-regulator gene and the NH$_2$-terminal encoding part of the gene can be sequenced. This locates the position of the AUG-startcondon. When useful restriction sites are absent in the promoter area, close to the AUG-startcodon, such a site (for instance BglII) can be introduced in that area via site-directed mutagenesis with an oligonucleotide according to standard methods (see also construction of recombinant plasmids, section 5*b*).

After such a mutagenesis the BglII-SalI fragment (containing the MAL-regulator gene without promoter area) and an EcoV-BamHI fragment (containing the ADHI promoter, sec also FIG. 7*d*, pGbiRR01) can be ligated together into pGb-RB2 (see FIG. 9), such that the MAL-regulator gene is under control of the ADHI promoter. This will yield plasmid pGb-iRBREG01. Sequence analysis using the dideoxychain methods with oligonucleotides on ssDNA as template, can easily confirm the correctness of the cloning steps and the orientation of the promoter.

It will be appreciated to recognize that the above-mentioned plasmids constructions merely serve as examples to illustrate the invention. Other promoters (preferably Saccharomyces) can be used (or other parts of the same promoter), other integration loci can be selected, other combinations of maltase, maltase, maltose permease the MAL-regulator (either under control of their own promoter or under control of another, preferably Saccharomyces promoter), can be made, using one or more integration sites in the yeast genome. It will ultimately lead to the optimal ratio of maltase and maltose permease activity present during the entire period of anaerobic fermentation.

Yeast Transformation

Transformation of yeast strains was carried out according to the method of Ito et al. (H. Ito, Y. Fukuda, K. Murata, A. Kimura (1983), J. Bacteriology 153, 163–168). It involves growing Saccharomyces in a standard yeast nutrient medium to a density of 1 to 25, desirably 4 to 10 OD$_{610}$ nm. The yeast cells are then harvested, washed and pretreated with chaotropic ions particularly the alkali metal ions, lithium, cesium or rubidium, particularly as the chloride or sulphate, more particularly the lithium salts, at concentrations about 2 mM to 1.0M, preferably about 0.1M. After incubatin the cells for from about 5 to 120 minutes, preferably about 60 minutes, with the chaotropic ion(s) the cells are then incubated with DNA for a short period of time at a moderate temperature, generally from about 20° C. to 35° C. for about 5 minutes to 60 minutes. Desirably, polyethylene glycol is added at a concentration of about 25 to 50%, where the entire medium may be diluted by adding an equal volume of a polyethylene glycol concentrate to result in the desired final concentration. The polyethylene glycol will be of from about 2000 to 8000 daltons, preferably about 4000 to 7000 daltons. Incubation will generally be for a relatively short time, generally from about 5 to 60 minutes. Desirably, the incubation medium is subjected to a neat treatment of from about 1 to 10 minutes at about 35° C. to 45° C. preferably about 42° C. For selection of transformants any useful marker may be used, such as phleomycin (D. Genilloud, M. C. Garrido, F. Moreno (1984) Gene 32, 225), hygromycin B (Gritz et al. (1983) Gene 25, 178) and aminoglycoside G418 (Jiminez et al. (1980), Nature, 287, 869).

When yeast cells have been transformed with integrating plasmids, integration was directed to the MAL-locus using BglII-digested DNA. The integrating plasmids used, contain two BglII sites, both in the maltase gene, 1.4 kb from each other. This generates double-stranded breaks, which are recombinogenic and stimulate interaction with homologous chromosomal DNA. The gap is repaired from chromosomal information during the integration event (T. L. Orr-Weaver, J. W. Szostak, R. Rothstein (1981) Proc. Natl. Acad. Sci. U.S.A. 78, 6334). The integration event yields one or a few copies of the plasmid vector (J. W. Szostak, R. Cou (1979) Plasmid 2, 536). The exact copy number in these transformants, used in $CO_2$-production experiments, has not been determined.

A scheme was a developed in order to order to obtain stable yeast transformants which do not contain heterologous DNA. Examples of heterologous DNA are the pTZ19R vector DNA and the selection genes conferring resistance to the antibiotics G418, phleomycin or hygromycin B. Briefly, the experimental set up was as follows (FIG. 12).

1) One-step gene disruption of a SIT4 gene via transformation of yeast with pGb-RBN3 digested will SflI Transformants have been selected for resistance to G418. The outcome was strain ApGb-RBN3, in which a SIT4 gene has been replaced by SIT4 gene, interrupted by the G418$^r$ gene under control of the ADHI promoter.

2) Strain λpGb-RBN3 was used as host strain in a cotransformation protocol with pUT332 and with pGb-RBRR01 digested with SfiI. pUT332 is a 2μ-derived episomal plasmid containing a gene confering resistance to phleomycin. The first selection in this cotransformation step was carried out on plates containing phleomycin (30 μg/ml). In a certain percentage of these phleomycin$^r$ yeast cells (in the order of 0.1 to 1%) the interrupted SIT4 gene (with pADHI/G418$^r$) has been replaced by the cotransformed SIT4 fragment containing altered maltose permease and maltase genes. This second gene-replacement event resulted in a yeast which is again sensitive to G418. To select for yeast cells in which this second gene-replacement has taken place, phleomycin$^r$ transformants were replica-plated onto plates containing G418 (300 μg/ml). In cells which did not grow, the G418$^r$ gene embedded between SIT4 gene sequences, has been replaced by the altered MAL-genes, embedded between SIT4 gene sequences.

3) Phleomycin$^r$ G418$^{sens}$ tranformants were then cured from the episomal plasmid pUT332 by growth on non-selective medium (i.e. without phleomycin) during 10–20 generations. The resulting transformant ApGb-pRBRR01 is sensitive to both phleomycin and G418 and contains no procaryotic sequences. All the integration events have been verified at the DNA level with Southern slot experiments (data not shown).

The resulting strain can be used as host in subsequent tranformations by use of another integration locus and/or—in case of yeast strains which are diploid or polypoid—as the other allele(s) of the SIT4 gene. Strain A is aneuploid and diloid for the chromosome containing the SIT4 gene. Both SIT4 genes of strain A were used as target site for gene replacement. This ultimately yielded transformant ApGb-p2RBRR01*1. The use of both alleles for integration most likely also increased the genetic stability of the transformant, since the second integration event removed the polymorfism at that locus. Such polymorphic regions are sensitive to gene conversions which can result in the loss of the integrated sequences. The transformant obtained in this way has been analysed with Southern plot techniques and shows the hybridization pattern as predicted from the gene disruption events at both SIT4 genes.

The constructed vector pGb-RB2 which served as starting plasmid for pGb-RBN3 and pGb-RBRR01, has several useful characteristics inspired by the following considerations:

1. Often a DNA segment has to be integrated, which is constructed by fusing a yeast promoter to a (yeast) coding region of another gene. Gene replacements are of course only readily obtained if the transforming fragments possess on both sides sequences homologous to a target-sequence in the genome. Therefore, a DNA segment has to be hooked onto the 3' end of the coding region (vide supra), which is derived from the same gene as the selected promoters. The disadvantage of this approach is that it requires many cloning manipulations, since not always the same promoter is used. In addition, often a strong promoter is selected, derived from a gene, which is functional at the stages of interest (during vegetative growth, anaerobic fermentation etc.). After integration of the engineered fragment one copy of this gene is made non-functional Therefore, we wish to direct gene replacement at a locus, which is not expressed during vegetative growth. We have selected the SIT4 gene (sporulation-induced transcribed sequence), whose expression is well studied by Gottlin-Ninja and Kaback (supra), but of course other SIT genes or in general non-coding segments are appropriate. When the DNA construct of interest is cloned into this SIT4 gene, the two resulting halves of the SIT4 gene serve as homologous ends for recombination.

One could argue that the chromosomal area, in which the gene is located, is transcriptionally inactive during vegetative growth as a result of a silencer, analogous to the one described for the HMR-locus (A. H. Brand et al. (1985) Cell 41, 41–48). This silencer DNA also represses transcription controlled by promoters, unrelated to mating-type promoters and can act on promoters 2600 bp away. Gottlin-Ninfa and Kaback (supra), however, have shown that the HIS3 gene is able to function during vegetative growth when integrated into the SIT4 gene.

2. To facilitate cloning manipulations, the SIT4 gene is provided with a synthetic piece of DNA, containing several unique restriction sites (polylinker with cloning sites). In addition, the polylinker contains at both sides stopcodons for translation in all possible reading frames (see FIG. 9). This is a safety-value to stop translation of any possible hybrid transcript, which may be synthesized across the junction. Such a hybrid transcript may otherwise code for a protein, whose effect is unknown.

3. To achieve homologous recombination, the DNA segment to be integrated contains at both ends restriction sites for NotI and SfiI, which both recognize 8 bp sequences. The frequency of occurrence of these restriction sites is very low and hence it is extremely unlikely, that a DNA segment to be cloned into the polylinker in the SIT4 gene, contains both recognition sites. Thus, once the DNA segment has been cloned into the SIT4 gene on plasmid pGb-RB2, restriction with NotI or SfiI liberates a DNA fragment, which can recombine by interacting with homologous sequences in the genome, i.e. at the SIT4 locus. Although the very ends are part of the NotI or SfiI site and hence not homologous, other studies have shown that—apparently by limited exonuclease digestion in the cell —these sequences are removed (e.g. H. Rudolph, J. Koenig-Ranseo and A. Hinnen (1985) Gene 36, 87–95).

4. As starting plasmid the commercially available plasmid pTZ19r, a pUC19 derivative is used. This vector has the advantage that it has a high copy number and that it possesses an origin of replication of the single-standed phase fl. This makes it very easy to isolate—after infection with a helper phage—single-standed DNA and to verify the DNA sequences across the junctions with the aid of primers. This greatly facilitates the detailed description of manipulated DNA.

It will be appreciated that it is possible to apply these improvements not only to bakers' yeast, but to other yeasts as well.

$CO_2$-production measurements a) in synthetic dough medium (Test A)

Yeast cells were incubated in YEPMS medium (1% yeast extract; 2% bactopepton; 3.75% maltose; 1.25% sucrose supplemented with 200 µg/ml G418). Growth was at 30° C. until late-log phase. Yeast cells were collected from 6 ml culture and resuspended in 8.8 ml synthetic dough medium. Composition of this medium (per liter): saccharose 4.6 g; maltose 64.37 g; $KH2PO_4$ 2.07 g; $MgSO_4.7H_2O$ 2.76 g; $(NH_4)_2SO_4$ 0.67 g; casamino acids 2.07 g; citric acid 4.02 g; $Na_3$ citrate 44.25 g; vitamin B1 9.2 mg; vitamin B6 9.2 mg; nicotinic acid 46 mg; Ca-D(+)-pantothenate 18.2 mg; biotin 0.23 µg. during 10 minutes the suspension was allowed to equilibrate in a 28° C. waterbath, with moderate stirring after which the flasks containing the yeast suspension were connected via a tube to a "gasburette".

This burette was filled with a solution containing per liter 20 ml indicator solution (1 g methylred; 0.5 g methylenblue; dissolved in 1 l 96% ethanol), 40 ml 1N $H_2SO_4$ and a trace of $CuSO_4$ (dissolved in $HNO_3$). The displacement of the volume of this solution in the burette is a measure for the $CO_2$-production, which was measured during 165 minutes.

In each set of experiments values of $CO_2$ production obtained have been corrected for environmental temperature and pressure to standard conditions of 28° C. and 760 Hg, respectively. In addition, a correction was made for the amount of yeast. The colorimetric readings at 600 nm of the culture have been used as correction factor in order to equalize the amount of yeast per $CO_2$ measurement.

b) in dough (Test B and B')

The $CO_2$ gassing curves of compressed yeast grown fed-batch wise on molasses was determined, in dough with no sugar added (lean dough) (Test B) or with 30% sugar (Test B'). The lean dough was prepared as follows: 1 g of compressed yeast (containing 28.5% dry matter), 34 ml salt solution A (1.25 g NaCl dissolved in 34 ml of distilled water) and 62.5 g flour were mixed in a Hobart apparatus for 30 seconds at speed 1 and 2 minutes at speed 2 so as to obtain a well developed dough.

The 30% sugar dough contained 2.0 g of compressed yeast (of 28.5% dry matter), 34 ml salt solution B (0.938 g NaCl in 34 ml of distilled water), 62.5 g flour and 18.75 g sucrose (i.e. 30% sugar with respect to flour). Mixing was as for lean dough.

The dough was then transferred to a round-bottom flask. Gas-production measurement was started 7.5 minutes after mixing, by connecting the flasks containing the dough via a tube to a gasburette (see section a) and performed during 165 minutes at 28° C. In the event that the dry matter content of the compressed yeast differs from the value indicated above, such yeast has been employed; however, the measured value of the $CO_2$ gassing power has then be corrected by multiplying the $CO_2$ gassing power by the ratio of the required dry matter content to the actual measured value. In each set of experiments, values of $CO_2$ production obtained have been corrected for environmental temperature and pressure to 28° C. and 760 mm Hg, respectively. In some cases additional calculations have been performed in which the gas values obtained have been corrected for the percentage of N of the fed-batch grown yeast (% N is an indication of the protein content). Similar percentages of improvements were found as without this last correction.

c) in dough (Test C and C')

The $CO_2$ gassing curves of dried yeast, such as instant dry yeast prepared according to procedures as described in U.S. Pat. No. 3,843,800 and U.S. Pat. No. 4,341,871 was determined in dough with no sugar added (test C) or with 30% sugar (test C'). These tests were performed in the same way as described in tests B and B' except that 300 mg of dried yeast (containing 96% dry matter) and 600 mg of dried yeast (containing 96% dry matter) were used in tests C and C', respectively. Prior to the test the yeast was mixed with the flour and incubated for 10 minutes at 28° C.

Enzymatic Analyses

The capacity to transport maltose by yeast cells was determined using (U-$^{14}$C)-maltose at a concentration of 15 mM as a substrate at 30° C. Details have been published by R. Serrano (Supra). Maltase (E.C. 3.2.1.20) was assayed for using p-nitrophenyl-α-D-glucopyranoside as a substrate in cell free extracts. The assay was carried out according to H. Halvorson and E. L. Elias, Biochim. Biophys. Acta (1958) 30, 28.

Substrate Consumption and Product Formation in Liquid Medium

The disappearance of maltose and glucose from liquid media was quantitated using standard HPLC-techniques. One liter of medium contained: 100 g maltose, 10 g glucose, 3.0 g $(NH_4)_2SO_4$, 4.0 g $MgSO_4.7H_2O$, 4 g $KH_2PO_4$, 4 g casamino acids (Difco), 4 g citric acid. $H_2O$, 45 g trisodiumcitrate.$2H_2O$, 10 mg vitamin 51, 10 mg vitamin H6, 40 mg nicotinic acid, 20 mg Ca-D(+)-pantothenate and 0.02 mg biotin. The pH was adjusted to 5.7. Two ml of medium was added to a suspension of yeast (20 mg dry weight/2.0 ml of distilled water). This mixture, termed medium A, was incubated at 28° C. Medium B was like medium A but contained 20 times more glucose. The experiment was carried out under anaerobic conditions.

Protein Determination

Protein of cell-free extracts and of whole cells was determined by the microbluret method of J. Goa, Scand. J. Chim. Lab. Invest. (1953) 5, 218. Ovalbumin served as a standard.

Keeping Quality

Compressed yeast was stored in closed plastic containers at 23° C. during 4 days. Keeping quality is defined as the percentage of remaining gassing power after this period.

Manufacture of Compressed Yeast

A culture of a yeast strain was grown in a series of fermentors. Cells were cultivated in 10 liter laboratory fermentors with a net volume of 6 liters. During the fermentation pH and temperature were maintained at desired values by automatic control. The fermentation recipe used is based on procedures described by G. Butscheck and R. Kautzmann, Die Refen, Band II Technologie der Hefen p. 501–591 (1962), Verlag Hans Carl. Nürnberg, FRC and those published by G. Reed and H. J. Peppler in Yesat Technology, the AVI Publishing Company Inc., Westport Conn., USA (1973). The cultivation conditions of the final fermentation were in particular:

molasses applied consisted of 80% by weight of beet molasses and 20% by weight of cane molasses, calculated on the basis of 50% sugar the required amount of phosphate was added in the form of mono-ammonium phosphate, prior to inoculation.

the temperature increased from 28° C. to 30° C. during the fermentation according to Table 1 nitrogen was supplied during the fermentation as a 10% solution of $NH_3$ in water according to Table 1.

pH was kept at 5.0 during the first 8 hours of the fermentation and increased thereafter according to Table 1 to 6.2 at the end of the fermentation.

Per kg of molasses containing 50% fermentable sugars 12 mg of vitamin B1 was added prior to inoculation.

The yeast obtained by this fermentation was concentrated and washed with tap water in a laboratory nozzle centrifuge. Yeast creams were compressed to a dry matter content varying between 26 and 32%.

The obtained protein content (%N×6.25) varied between 42–55% of dry weight as a consequence of different quantities of ammonia applied during the fermentation.

TABLE 1

Fermentation recipe used for the fed-batch wise production of baker's yeast

| Hours after inoculation | Molasses supply (% of total amount added) | pH | T (°C.) | Ammonia supply (% of total amount added) |
|---|---|---|---|---|
| <0 | 7 | 5 | 28.0 | 0 |
| 0–1 | — | 5 | 28.0 | 0 |
| 1–2 | 5 | 5 | 28.0 | 0 |
| 2–3 | 6 | 5 | 28.5 | 1 |
| 3–4 | 8 | 5 | 28.5 | 7 |
| 4–5 | 8 | 5 | 29.0 | 11 |
| 5–6 | 8 | 5 | 30.0 | 11 |
| 6–7 | 10 | 5 | 30.0 | 12 |
| 7–8 | 10 | 5 | 30.0 | 15 |
| 8–9 | 10 | 5.3 | 30.0 | 17 |
| 9–10 | 10 | 5.6 | 30.0 | 17 |
| 10–11 | 10 | 5.9 | 30.0 | 10 |
| 11–12 | 8 | 6.2 | 30.0 | 0 |

EXAMPLE 1

Figure 3:
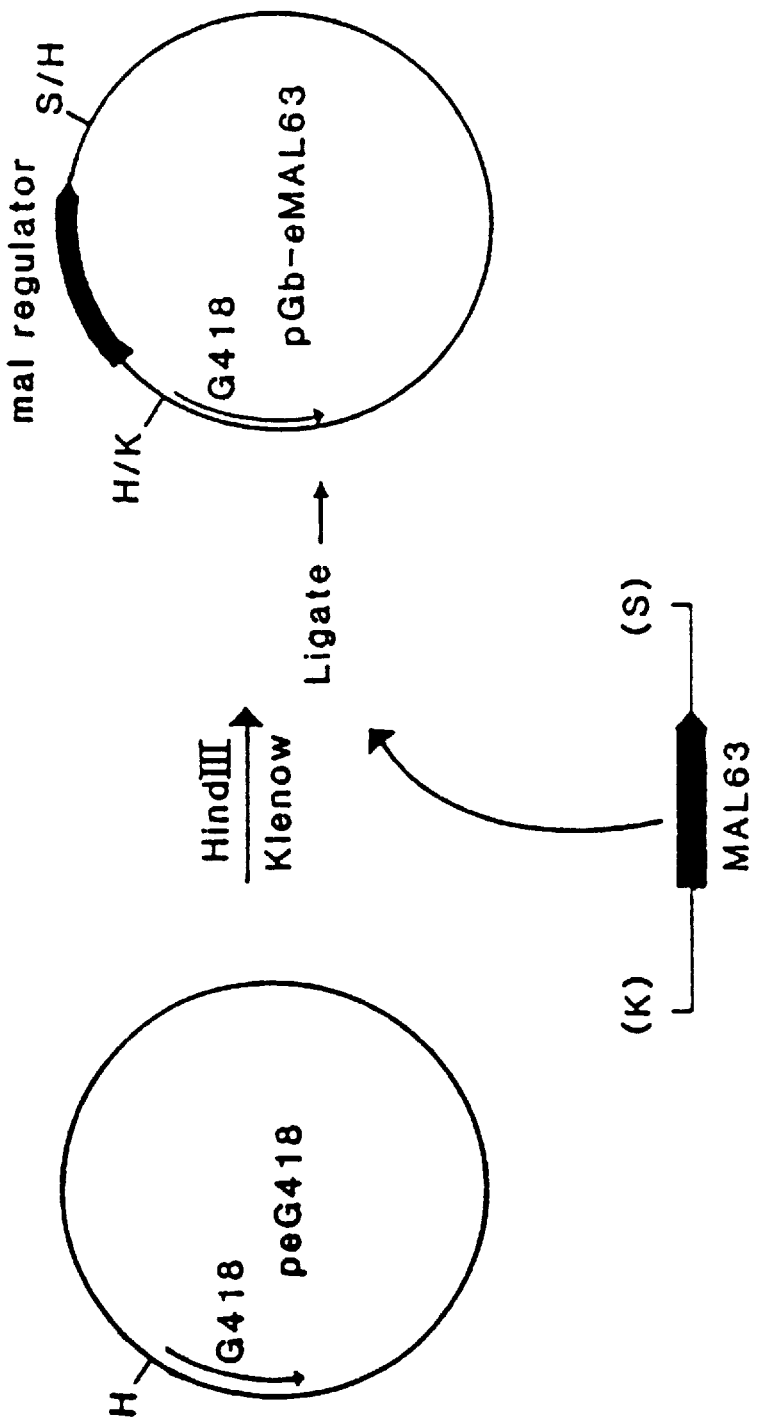
FIG. 3 describes the construction of plasmid pGb-eMAL63. Plasmids are drawn schematically and not to scale. Abbreviations: (K), filled-in KpnI site; (S), filled-in SalI site; Klenow, large subunit DNA polymerase; H, HindIII. See also description of FIG. 1.

$CO_2$-production of yeast transformed with $2\mu$-derived plasmids containing genes derived from the MAL6 locus Commercial baker's yeast strains A and C have been transformed with pGb-eMAL6g (maltose permease and maltase, see FIG. 1), pGb-eMAL61 (maltose permease, see FIG. 2) and pGb-eMAL63 (MAL-regulator, see FIG. 3). The MAL genes still contain their original promoters. The nomenclature of the transformed yeast strains is as follows: ApeG418 denotes strain A transformed with peG418. Other transformed strains have been indicated in an analogous way. The effects of these plasmids on the $CO_2$-production in synthetic dough medium is summarized in Table 2. The host strain, transformed with starting peG418 (see FIG. 1) serves as a reference, since we have found that the mere presence of a multicopy plasmid has a negative effect on the gas production.

All transformants display major $CO_2$ production improvements, relative to the control. The combination of extra copies of both maltose permease and maltase genes gives the highest enhancement, about 40% in strain A and 18% in strain C.

Transformants ApGb-eMAL6g and CpGb-eMAL6g have also been tested in dough with no added sugar. In this case the yeast was grown fed-batch wise on molasses.

Again, major improvements in $CO_2$ production were obtained (Table 3).

TABLE 2

Gas production of strain A and strain C transformed with $2\mu$-derived MAL plasmids, relative to the vector-transformed strains. $CO_2$ production was measured in synthetic dough medium (see experimental procedures) and corrected to 285 mg dry matter. Data are mean values of several experiments.

| strains | 100 minutes | 165 minutes |
|---|---|---|
| ApeG418 | 100 | 100 |
| ApGb-eMAL6g | 157 | 141 |
| ApGb-eMAL61 | 144 | 123 |
| ApGb-eMAL63 | 119 | 115 |
| CpeG418 | 100 | 100 |
| CpGb-eMAL6g | 121 | 118 |
| CpGb-eMAL61 | 117 | 114 |

TABLE 3

Relative gas production in dough of strains A and C, transformed with $2\mu$-derived plasmids peG418 and pGb-eMAL6g, $CO_2$ production was corrected to 285 mg dry matter.

| strains | 60 minutes | 100 minutes | 120 minutes | 165 minutes |
|---|---|---|---|---|
| ApeG418 | 100 | 100 | 100 | 100 |
| ApGb-eMAL6g | 125 | 125 | 125 | 121 |
| CpeG418 | 100 | 100 | 100 | 100 |
| CpGb-EMAL6g | 151 | 141 | 138 | 129 |

EXAMPLE 2

$CO_2$ production of yeast strains transformed with integrating plasmids containing recombinant maltase and/or maltose permease genes Parental yeast strain A has been transformed with pGb-iA32/G418 (main feature: ADH1/maltose permease; see FIG. 6) and pGb-iRRo1 (main feature: ADH1/maltose permease and EPIαA/maltose; see FIG. 7).

Parental strain A and both integrative transformants are grown fed-batch wise on molasses similar to the commercial aerobic fermentation (see Table 1). After harvesting the cells, $CO_2$ production is measured in a standard dough test with no sugar added. The gas production, as analysed in this test, is summarized in Table 4. Integration of pGb-iA32/G418 into the chromosome of strain A improves gas production in dough significantly. The relative improvement varies somewhat depending on time of measurement (see Table 4). When in addition to an altered maltose permease gene an altered maltase gene is integrated in the chromosome of commercial strain A using pGb-iRRo1 gassing power is even further improved. In this typical experiment about 30% more $CO_2$ is produced after 165 minutes in a lean dough, which corresponds to a level of about 410 ml $CO_2$/285 mg dry weight of yeast.

In a 30% dosage sugar dough no substantially differences in $CO_2$ production of the transformants were noticed compared to the parental strain (about 190 ml $CO_2$/285 mg dry weight of yeast).

The obtained improvement in leavening activity is maintained during storage at 23° C. The loss of leavening activity during storage is virtually identical for parental strain A and the novel strain (see Table 5).

TABLE 4

Relative gas production of strain A and its rDNA derivatives provided with altered maltase and/or maltose permease genes. Gas values have been corrected to 285 mg dry matter. No sugar was added to the dough.

| Strain | 60 minutes | 100 minutes | 120 minutes | 165 minutes |
|---|---|---|---|---|
| A | 100 | 100 | 100 | 100 |
| ApGb-iA32/G418 | 113 | 115 | 115 | 111 |
| ApGb-iRRo1 | 131 | 136 | 138 | 133 |

TABLE 5

Keeping quality of strain A and its rDNA derivatives provided with altered maltase and/or maltose permease genes. Leavening activity was measured as in Table 4 after keeping of compressed yeast at 23° C. for 4 days.

| Strain | keeping quality (% of original leavening activity) |
|---|---|
| A | 90 |
| ApGb-iA32/G418 | 91 |
| ApGb-iRRo1 | 88 |

EXAMPLE 3

$CO_2$ production of a yeast strain which contains recombinant maltase and maltose permease genes and no heterologous DNA.

Parental strain A has been genetically modified such that a pADHI/maltose permesae gene and a pEF1αA/maltase gene were introduced into the SIT4 gene on both homologous chromosomes. This strain, abbreviated ApGb-p2RBRR01 #1, has been constructed using the methods and plasmids as described previously (see sections of transformation and construction of plasmid of pGb-RBN3 (FIG. 10) and pGb-RBRR01 (FIG. 11) and the general scheme of transformation via gene-replacement. Parental strain A and the homologous transformant ApGb-p2RBRR01 #1 have been grown fed-batch wise on molasses similar to the commercial aerobe fermentation (see Table 1). After harvesting the cells, $CO_2$ production is measured in a standard dough test with no sugar added.

Table 6 summarizes the results. In the "lean" dough the improvement is about 18% after 165 minutes, which corresponds to a level of about 367 ml $CO_2$/285 mg dry weight of yeast. This strain contains two copies each of a maltose permease gene under control of the ADHI promoter and a maltase gene under control of the EF1αA promoter. In Table 4 is shown that strain ApGb-iRR01 has an improvement of about 30%. An initial estimation of the number of pGb-iRR01 molecules integrated into a MAL-locus of strain A, gives a copy number of integrated plasmid molecules of at least 3. By further increasing the copy number of altered maltose permease and maltase genes in strain ApGb-p2RBRR01 #1 (e.g. by integration in other sporulation-specific genes) a homologous transformed yeast strain can be obtained with at least similar gas production levels as strain ApGb-iRR01.

TABLE 6

Relative gas production of strain A and its homologous rDNA derivative provided with altered maltase and maltose permase genes. Gas values have been corrected to 285 mg dry matter. No sugar was added to the dough.

| Strain | 60 minutes | 100 minutes | 120 minutes | 165 minutes |
|---|---|---|---|---|
| A | 100 | 100 | 100 | 100 |
| ApGb-p2RBRR01#1 | 124 | 128 | 127 | 118 |

EXAMPLE 4

Enzyme activities and substrate uptake rates of yeast strains transformed with integrating plasmids containing recombinant maltase and/or maltose permease genes As described above, the expression of maltose permease and maltase is subject to maltose induction and glucose repression. This phenomenon is shown in FIG. 13 for wild-type cells of strain A. Specific activities of maltose permease and maltase do not increase until most of the glucose has been utilized.

The activity of maltose permesae at the onset of dough-rise is increased by introduction of an altered maltose permease gene into the yeast genome (strain ApGb-iA32/G418) as shown in FIG. 14.

Surprisingly, activities of maltase were increase as well in this construct (FIG. 15). This novel strain ApGb-iA32/A418 fermented maltose more rapidly than the parental strain A in medium A which contains maltose as main carbon and energy source (FIG. 16). In medium B containing glucose as main carbon and energy source this effect was less pronounced (FIG. 17).

In addition to an altered maltose permease gene an altered maltase gene was integrated in the chromosome yielding strain ApGb-iRRo1. This strain fermented maltose at an even higher rate in medium A (FIG. 16) and also in medium B (FIG. 17). Despite the high extra extracellular concentration of glucose considerable amounts of maltose were metabolized by this novel strain. Strain ApGb-iRRo1 exhibited higher specific activities of maltase and maltose permesae during dough-rise than parental strain And strain ApGb-iA32//G418 (FIG. 14 and 15).

What is claimed is:

1. A transformed yeast comprising:
   at least one DNA construct present in said transformed yeast as a result of transformation, said DNA construct comprising at least one gene encoding a protein promoting at least one of the uptake of a sugar substitute and initial metabolic conversion of a sugar substrate subsequent to uptake, the gene or genes being expressed in said yeast and encoding a maltose permease, maltase, or a maltose regulatory protein;
   said parent yeast having a corresponding gene encoding a protein having the same function as that of the protein encoded by said gene;
   said transformed yeast having an enhanced rate of sugar fermentation as compared to said parent yeast.

2. The transformed yeast according to claim 1 wherein said at least one gene is an homologous gene.

3. The transformed yeast according to claim 1 wherein said gene or genes are under the transcriptional control of a promoter which is insensitive to glucose repression and maltose induction.

4. The transformed yeast according to claim 1 wherein said construct comprises two of said genes and wherein said genes are under the transcriptional control of at least one of alcohol dehydrogenase I and translation elongation factor promoter.

5. The transformed yeast according to claim 4 wherein said alcohol dehydrogenase I promoter and said translation elongation factor promoter are derived from a yeast belonging to the genus Saccharomyces.

6. The transformed yeast according to claim 1 wherein said DNA construct is a portion of an episomal element.

7. The transformed yeast according to claim 1 wherein said DNA construct is integrated into a chromosome of said yeast.

8. The transformed yeast according to claim 1 which comprises at least two of said DNA constructs.

9. The transformed yeast according to claim 1 wherein said transformed yeast is free of heterologous DNA.

10. A yeast having a moisture content of 3 to 8% which is produced by drying the transformed yeast according to claim 1.

11. The yeast according to claim 10, wherein said yeast belongs to the genus Saccharomyces.

12. The yeast according to claim 11, wherein said yeast is *Saccharomyces cerevisiae*.

13. A compressed, instant dry or active dry yeast produced from the transformed yeast according to claim 1.

14. An instant dry or an active dry yeast produced by drying the compressed yeast according to claim 13.

15. A compressed yeast, produced from the transformed yeast according to claim 1 wherein said compressed yeast provides a gas production of at least 340 ml/285 mg dry weight of yeast in 165 minutes in Test B and a gas production of at least 170 ml/285 mg dry weight of yeast in 165 minutes in Test B'.

16. A comprised yeast, produced from the transformed yeast according to claim 1, which shows a gas production of at least 400 ml/285 mg dry weight of yeast in 165 minutes in Test B and a gas production of at least 190 ml/285 mg dry weight of yeast in 165 minutes in Test B'.

17. A compressed yeast, produced from the transformed yeast according to claim 1, which shows a gas production of from 400–500 ml/285 mg dry weight of yeast in 165 minutes in Test B.

18. A dried yeast, produced from the transformed yeast according to claim 1, which shows a gas production of 310–360 ml/285 mg dry weight of yeast in 165 minutes in Test C and a gas production of 145–195 ml/285 mg dry weight of yeast in 165 minutes in Test C', respectively.

19. A dough or similar product which comprises the transformed yeast according to claim 1.

20. A method for producing bread said method comprising:
preparing said bread from the dough according to claim 19.

21. A method for producing a leavened flour product, alcoholic beverage or other alcoholic product, said method comprising:
contacting a raw material for said leavened flour product, alcoholic beverage or other alcoholic product with the transformed yeast according to claim 1, under conditions whereby said leavened flour product, alcoholic beverage or other alcoholic product is produced from said raw material.

22. The transformed yeast according to claim 1 wherein said yeast is of the genus Saccharomyces and said DNA construct comprises at least one gene selected from a maltase, a maltose permease or a maltose regulatory protein.

23. A transformed yeast comprising a DNA construct substantially free of prokaryotic DNA, said DNA construct comprising at least one of the following genes: maltase, maltose permease or a MAL regulator protein wherein said gene(s) are capable of expression in said yeast; said parent yeast having a corresponding gene encoding a protein having the same function as that of the protein encoded by said gene; wherein said transformed yeast has an increased rate of fermentation of maltose into ethanol and carbon dioxide when said DNA construct is expressed.

24. The transformed yeast according to claim 23 wherein maltase is under transcriptional control of a translation elongation factor (EF1αA) promoter.

25. The transformed yeast according to any of claim 23 and 24 wherein maltose permease is under transcriptional control of an alcohol dehydrogenase I (ADHI) promoter.

26. The transformed yeast according to any one of claims 23 and 24 wherein said promoters are derived from a yeast belonging to the genus Saccharomyces.

27. The transformed yeast according to claim 23 wherein said transformed yeast is of the genus Saccharomyces.

28. A method for producing a transformed yeast having an enhanced rate of sugar fermentation as compared to a parent yeast, said method comprising:
introducing into said parent yeast at least one DNA construct which comprises at least one gene encoding a protein promoting at least one of the uptake of a sugar substrate and initial metabolic conversion of a sugar substrate subsequent to uptake, the gene or genes being expressed in said yeast and encoding a maltose permease, maltase, or a maltose regulatory protein,
said parent yeast having a corresponding gene encoding a protein having the same function as that of the protein encoded by said gene.
whereby said transformed yeast is produced.

29. The method according to claim 28, wherein said DNA construct comprises at least two of said genes.

30. The method according to claim 28, wherein said DNA construct comprises two of said genes, which are under transcriptional control of at least one of alcohol dehydrogenase I (ADHI) and translation elongation factor (EP1αA) promoters.

31. The method according to claim 28, wherein said gene or genes are under transcriptional control of a promoter which is insensitive to glucose repression and maltose induction.

32. The method according to claim 30 or claim 31, wherein said promoters are derived from a yeast belonging to the genus Saccharomyces.

33. The method according to claim 28, wherein said DNA construct is a portion of an episomal element.

34. The method according to claim 28, wherein said DNA construct is integrated into a chromosome of said yeast.

35. The method according to claim 28, which comprises the introduction of at least two of said DNA constructs.

36. The method according to claim 28, wherein said transformed yeast is free of heterologous DNA and wherein said genes are integrated into the chromosome using gene replacement.

37. The method according to claim 28, wherein said DNA construct further comprises a sequence of a sporulation-specific gene and, as a result of transformation, a chromosomal sporulation-specific gene is replaced by said DNA sequence comprising a sequence of said sporulation-specific gene and at least one gene encoding a protein promoting at least one of the uptake of a sugar substrate and metabolic conversion of a sugar substrate subsequent to uptake.

38. A method for producing a dough said method comprising:
   contacting ingredients for said dough with a transformed yeast produced according to the method of claim 28 under conditions whereby a dough is produced.

39. A method for producing an alcoholic product, said method comprising:
   contacting ingredients for said alcoholic product with a transformed yeast produced according to the method of claim 28 under conditions whereby alcohol is produced.

40. The method according to claim 39 wherein said alcoholic product is a beverage.

41. The method according to claim 28, wherein said yeast belongs to the genus Saccharomyces.

42. The method according to claim 28 wherein said yeast is of the genus Saccharomyces.

43. A vector selected from the group consisting of
   pGb-RBRRO1,
   pGb-RBN3, and
   pGB-RBREGO1.

44. A yeast selected from the group consisting of
   *Saccharomyces cerevisiae* strain CpGb-eMAL61, and
   *Saccharomyces cerevisiae* strain ApGb-p2RBRR01#1.

45. A transformed yeast comprising a DNA construct substantially free of prokaryotic DNA, said DNA construct comprising at least one of the following genes; maltase, maltose permease or a maltose regulatory protein wherein said gene(s) are capable of expression in said yeast;
   the parent yeast which does not comprise said DNA construct having a corresponding gene encoding a protein having the same function as that of the protein encoded by said gene;
   wherein said transformed yeast has an increased rate of sugar fermentation as compared to said parent yeast.

* * * * *